(12) United States Patent
Mansmann

(10) Patent No.: US 8,814,871 B2
(45) Date of Patent: Aug. 26, 2014

(54) SURGICAL TOOLS WITH EXTENDIBLE AND ROTATABLE ACCESSORY COMPONENTS

(75) Inventor: Kevin A. Mansmann, Paoli, PA (US)

(73) Assignee: Formae, Inc., Paoli, PA (US)

(*) Notice: Subject to any disclaimer, the term of this patent is extended or adjusted under 35 U.S.C. 154(b) by 644 days.

(21) Appl. No.: 11/521,939

(22) Filed: Sep. 15, 2006

(65) Prior Publication Data

US 2007/0118135 A1    May 24, 2007

Related U.S. Application Data

(60) Provisional application No. 60/739,467, filed on Nov. 23, 2005.

(51) Int. Cl.
*A61B 17/00* (2006.01)
*A61B 17/16* (2006.01)
*A61B 17/32* (2006.01)

(52) U.S. Cl.
CPC ............. *A61B 17/1633* (2013.01); *A61B 17/16* (2013.01); *A61B 17/1624* (2013.01); *A61B 2017/1602* (2013.01); *A61B 17/32002* (2013.01); *A61B 17/1662* (2013.01); *A61B 2217/005* (2013.01)

USPC ............................................................ 606/80

(58) Field of Classification Search
USPC ...................... 606/79, 80, 84, 86 R
See application file for complete search history.

(56) References Cited

U.S. PATENT DOCUMENTS 5,425,376 A * 6/1995 Banys et al. .................. 600/566
5,601,583 A * 2/1997 Donahue et al. .............. 606/170

* cited by examiner

*Primary Examiner* — Sameh Boles
(74) *Attorney, Agent, or Firm* — Duane Morris LLP

(57) ABSTRACT

Surgical tools are disclosed for minimally-invasive planing of bone surfaces that will support prosthetic implants, such as cartilage-repair implants. Such planing tools must create smooth surfaces that will closely fit the anchoring surface of an implant. Such tools can use a rotating cylindrical burr, partially covered by a cowl having adjustable components to control grinding depth and bone curvature. Burrs can be mounted on the ends of rotating shafts, or they can be angled, using drive-coupling interfaces. In other embodiments, shaver or burr tools can be supplemented by accessory-type devices (such as suction tubes, cautery tips, and pinchers) that can be extended beyond the normal working tip of a tool, to enable additional functions that will be useful during surgery.

7 Claims, 20 Drawing Sheets

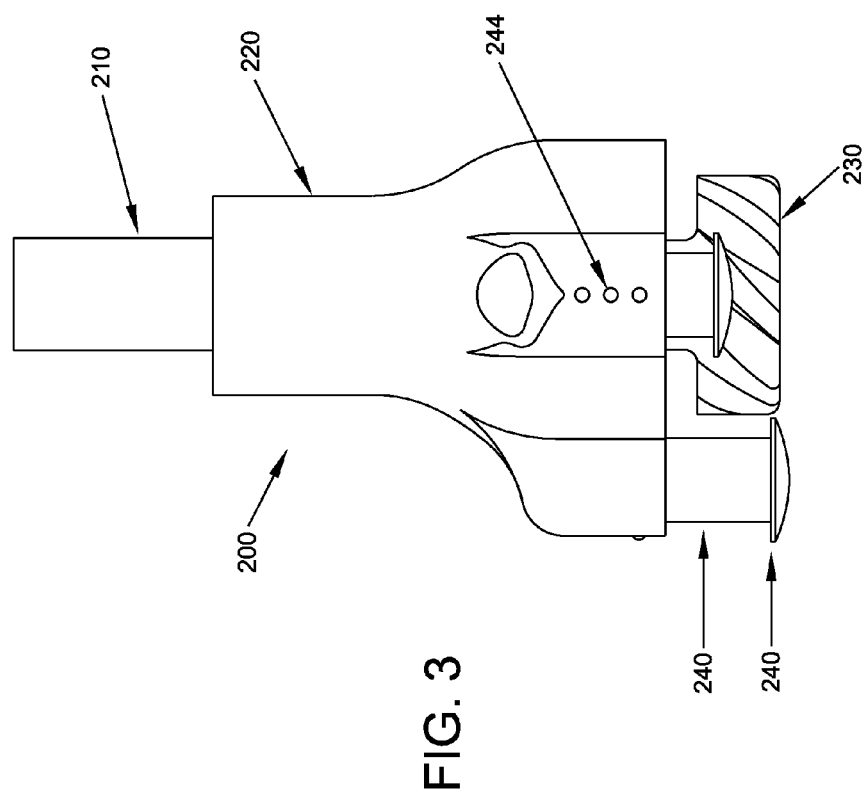

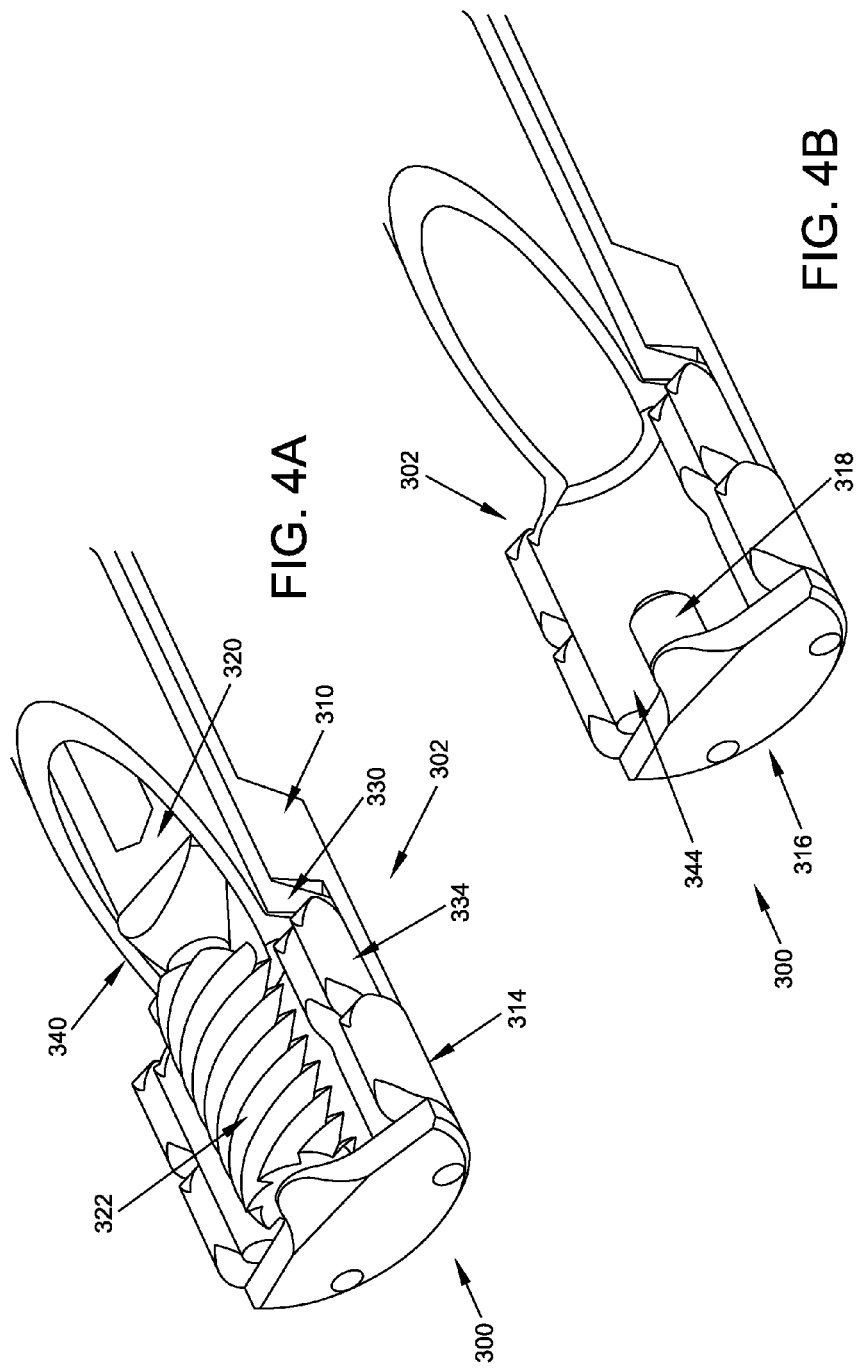

SURGICAL TOOLS WITH EXTENDIBLE AND ROTATABLE ACCESSORY COMPONENTS

RELATED APPLICATION

This application claims priority under 35 USC 119(e) based on provisional application 60/739,467, filed Nov. 23, 2005.

BACKGROUND OF THE INVENTION

This invention is in the field of surgical tools for shaping bones, for purposes such as repairing or replacing damaged cartilage in mammalian joints.

In certain types of surgery (including but not limited to orthopedic surgery to repair damaged cartilage in a knee, hip, shoulder, or other joint), it is necessary to prepare a bone surface, before the surface can receive and support an implant in a stable, secure manner that preferably will last for decades. In such surgery, arthroscopic or other "minimally-invasive" methods and tools generally are preferred whenever possible, since they minimize tissue damage, recovery times, etc.

Relevant art in the field of arthroscopic tools that can be used to manipulate bone surfaces (and other types of minimally invasive tools, for manipulating other types of internal tissues) can be found in numerous US patents in various subclasses within Class 606, including subclasses 79, 80, and 96; Examples include U.S. Pat. No. 6,884,246 (Sonnabend et al 2005), U.S. Pat. No. 6,120,507 (Allard et al 2000), U.S. Pat. No. 6,358,253 (Torrie et al 2002), and U.S. Pat. No. 5,817,095 (Smith 1998). However, most such art involves items that are either: (i) designed to create holes for anchoring devices, or for similar non-planar sculpting of bones surfaces; or, (ii) designed for use in "open joint" surgery, rather than arthroscopic surgery. The Applicant herein is not aware of any patents or articles describing tools having designs comparable to those shown herein, to facilitate the arthroscopic preparation of a smooth (or "planed") bone surface, or for similar uses with other tissues.

Various other types of tools have been developed for arthroscopic, laparoscopic, and other types of minimally-invasive surgery, and they are illustrated in the catalogs and websites of various tool sellers, including Smith and Nephew (www.smith-nephew.com) and Stryker (www.stryker.com). The most relevant tool known to the Applicant herein is usually called a "rotary basket punch". It uses a scissors-type grip, or a rotational squeeze-operated grip, with a long thin shaft containing a rotating rod inside a nonrotating sleeve. At the end is a small sharp blade affixed to the rotating rod. When a surgeon squeezes the scissors-type grip, a gear mechanism causes the rod to rotate, which causes the blade at the end to pass through an arc of travel. In this manner, the blade will cut through a rounded arc of soft tissue, such as for biopsy removal, to cut away a piece of torn cartilage, etc. That tool is of interest, because of the gearing mechanism that causes the manipulator device at the "working end" of the tool (i.e., the tip of the tool that enters a patients body or limb) to pass through a circular arc, when the grip is squeezed and closed by a surgeon. However, the existence of a rotating component, in a rotary basket punch tool, is the only substantial similarity between that type of prior art tool, and the new types of tools described below.

Several terms need to be clarified at this point, and it should be understood that other similar or analogous terms can also be used if desired. These terms are intended to be used in common and conventional ways, as used by surgeons who use these types of tools. However, it should be noted that the usage of some terms, including usage among surgeons and in articles and textbooks, can vary, in ways that usually reflect various lay meanings and inferences. As one example, some people and articles refer to the "handle" of a tool as including that portion of a tool shaft which does not enter a person's body or limb, as well as any other appurtenances that are intended for gripping and that are coupled to the toolshaft. However, other people and articles refer to the "handle" of a tool as excluding any portion of a tool shaft, and being limited only to gripping components that are coupled to a tool shaft. As another example, some people refer to a mammalian "body" as including only the shoulders, chest, abdomen, hips, etc; other also include the head but not the limbs; and other also include the limbs. Those types of differences and distinctions are merely semantic in nature, and anyone who understands how such tools function and are used can readily interpret and understand how the various terms used herein can be applied to the modified tools described and illustrated herein.

As used herein, "handle" (which could also be referred to as the grip, base, etc.) includes any portion of a tool that a surgeon can use to grip, move, and otherwise manipulate the tool. In minimally-invasive surgery, the handle normally remains outside the patient's body. If desired, a handle can include or be supplemented by one or more attachments, such as one or more gripping handles oriented perpendicular or otherwise angled with respect to the tool shaft (as in the types of rotary basket punches mentioned above), to provide a surgeon with better control over positioning, motion, and rotation of the tool.

The term "handle end" is also used herein in a broad sense. It is not limited to the very tip (or base) of a handle; instead, as used herein, a tool having a shaft should generally be understood as being divided into three portions, which are the handle end, the working end, and some length of shaft which separates the handle end, from the working end.

As use herein, the "base" of a handle is also used broadly. It is not limited to a single component that actually touches and sits next to a cable end, from a drive unit. Instead, it can include additional components that form an assembly that occupies the end of a handle. The specific component that actually touches the end component of a flexible cable from a drive unit, when the tool is coupled to such a drive unit, can be called the root, the collar, or similar terms.

A drive unit is a mechanical system that remains outside a patient's body, which provides one or more flexible cables that can provide drive power, and suction capability, to any suitable tool affixed to the end of such a cable. Suitable drive units, made by companies such as Smith & Nephew or Stryker, are well-known, and are already owned and used by any hospital or clinic where orthopedic surgery is routinely done. Each of those two companies uses its own proprietary interface at the ends of its drive cables, to promote the sale and use of tool heads made and sold by that company. Accordingly, any tool described herein should be designed to be coupled to a type of drive interface that already is in widespread use among hospitals and clinics.

The terms "head", "working head", and "tip" are used interchangeably herein, to refer to a device (which in most cases will be an assembly or subassembly) positioned at or near the tip of the shaft. This subassembly will enter a patient's body, when the tool is in use. It typically will include one or more components such as a grinding burr, one or more blades, the tip of a suction tube, a cautery device, any cowl component(s) that may be present, any adjustable or other appurtenances that are mounted to or that interact with the cowl component, etc. As used herein, "cautery" can also be called coagulation, and it can use either electrical voltage or radiofrequency energy to close and seal blood vessels, etc.

The term "manipulator component" refers to a component at the working end of a tool, which alters or otherwise manipulates tissue, usually by means of direct contact (such as a burr, blade, pincher, etc.), or by emitting heat or other energy (such as a cautery tip, often referred to by surgeons as "Bovies", after a widely-used brand of cautery tips).

The term "sleeve" is used to refer to any and all non-rotating, non-drive-belt components that are positioned between a tool handle or base, and the working head of the tool. The sleeve normally will include or provide suction means, and it will enclose and protect a drive mechanism. Most rotating devices are driven by a rotating shaft, flexible drive belt, miniaturized motor, etc.; it should also be noted that reciprocal or other forms of motion can be used to carry out a planing or similar procedure, if desired, and such motion can be provided by other types of miniaturized systems.

Terms such as "cylindrical" and "generally cylindrical" are used interchangeably herein, for convenience, and include any type of grinding burr that has a surface shape designed to rotate around a longitudinal axis, when performing a planing-type procedure. Such burrs can have modified cylindrical shapes (such as, for example, cylinders having convex or concave shapes). Similarly, a cylindrical burr can have a combination of both (i) an abrasive or grinding surface, and (ii) a smooth and nonabrasive surface, which can have an enlarged diameter if desired, to serve as a "stop", detente, or other type of positioning or control device.

Planing Tools

One primary focus of this invention is on planing tools that which can be used to prepare a bone surface so that it is ready to receive and stably support a prosthetic implant. As used herein, terms such as "planed" or "planar" refer to a bone surface that has been prepared (or worked, machined, treated, or similar terms) in a manner that provides it with a relatively smooth surface. A planed surface generally should be free of burrs, ridges, protrusions, crevices, and other irregularities that could interfere with stable and durable anchoring (or fixation, attachment, etc.) of a prosthetic device to the bone surface. As used herein, terms such as planing, planed, or planar are not limited to the mathematical definition of a plane, which refers to a truly flat and two-dimensional surface. Instead, planing tools also can be used to prepared smooth rounded surfaces on the condyles or other rounded portions of various bones, as occur on femoral runners, in ball-and-socket joints such as hips and shoulders, and in other types of joints. Terms such as "rounded" or "curved" are not limited herein to spherical shapes, and can includes shapes such as cylindrical, elliptical, curvilinear, etc.

Accordingly, the term "planing tools" as used herein refers to tools designed to create relatively smooth flat, rounded, or curved surfaces on bones, including but not limited to bone surfaces that are being prepared to receive and support surgical implants. Planing tools are different and distinct from tools such as drills, routers, etc., which are used mainly to create alterations (such as holes, grooves, etc.) in a prepared surface. However, it should be noted that at least some types of planing tools also can be referred to by other terms, such as "shaving tools" or "shavers". The use of that term arises from the similarities between surgical shavers, and the types of shavers used to remove whiskers, leg hair, etc., to leave behind smooth-looking skin.

For purposes of illustration, the description below focuses on tools that can be used for arthroscopic preparation of bone surfaces that will receive implants designed to repair or replace damaged cartilage, in joints such as knees, hips, shoulders, etc. It will be recognized by those skilled in the art that these types of tools also can be adapted and used for other types of surgery as well, including spinal surgery, surgery to correct genetic malformations or bone-related diseases or injuries, surgery to implant other types of medical devices (such as devices for electrostimulation of muscles or nerves, devices for long-term drug release, devices to sequester transplanted cells to prevent immune rejection, etc.), and surgery to remove or alter the shapes of benign tumors and other unwanted growths.

In particular, it should be noted and emphasized that certain embodiments described below can be adapted for use on a variety of tools used today in a wide variety of arthroscopic, laparoscopic, exploratory, biopsy-gathering, and other surgical procedures. In general, these new types of tools provide an "extendible manipulator component" that can be extended in a linear direction, under the control of a surgeon, beyond their initial mounting or entry position. Accordingly, this new class of mechanisms can allow a surgeon to move an extendible device such as a suction tube, a cautery tip, or a set of pinchers, some distance (such as up to a centimeter or more) beyond what would otherwise be the "working tip" of a nonextendible manipulator component, such as a grinding burr or a shaver orifice. As will be recognized by surgeons, the ability to temporarily extend a device such as a suction tube, cautery tip, or set of pinchers, out beyond the normal tip of a tool, whenever desired during a surgical operation, can enable a number of new and highly useful functions that extend well beyond repairing cartilage, or preparing bone surfaces to receive implants.

Accordingly, one object of this invention is to disclose a new class of planing tools for arthroscopic, orthopedic, or other surgical use, to create smoothed bone surfaces (which can be flat, rounded, or curvilinear) that can support the anchoring of cartilage-repair or other surgical implants.

Another object of this invention is to disclose new methods for creating or improving flat or smoothly-rounded surfaces on bones, prior to implantation of surgical or medical devices, such as cartilage repair implants.

Another object of this invention is to disclose a new class of tools for creating or improving flat or smoothly-rounded surfaces, on various types of tissues other than bones.

Another object of this invention is to disclose a new class of surgical tools that have an additional functional device (such as a suction tube, cautery device, or set of pinchers) that can be extended beyond the normal nonextendible working tip of the tool, under the control of a surgeon.

These and other objects of the invention will become more apparent through the following summary, drawings, and description.

SUMMARY OF THE INVENTION

Surgical tools are disclosed for arthroscopic or other minimally-invasive preparation of bone surfaces, so that a bone surface can securely support a prosthetic implant, such as an implant for replacing or regenerating cartilage in a joint such as a knee, hip, shoulder, etc. These tools are referred to as "planing" tools, designed to create relatively smooth and regular flat or curved surfaces that will closely fit the anchoring surface of an implant.

In one embodiment, this type of planing tool comprises a rotating cylindrical burr, mounted at or near the working end of a shaft which has a handle at the other end. The burr is covered around most of its circumference by a cowl assembly, and the partially-exposed burr is used for a grinding and planing operation. The burr's grinding depth can be adjusted, such as by rotating threaded struts spaced around the perimeter of the cowl, or by using one or more levers on the tool handle to rotate one or more partial cowl components at the working tip.

In other embodiments, shaver or burr tools can be supplemented by additional devices (such as suction tubes, cautery tips, and closable pinchers) that can be extended beyond the normal working tip of a tool, to enable additional functions that will be useful during various types of surgery.

BRIEF DESCRIPTION OF THE DRAWINGS

FIG. 3 is side perspective view of another type of planing tool with a flat grinding surface at one end of a burr, rather than a cylindrical grinding surface along the length of a burr.

FIGS. 4A (with the burr shown) and 4B (with the burr removed, to better illustrate other components) depict two partial cowls, mounted at the ends of rotatable hollow shafts within a tool shaft. Under the control of levers mounted on the tool handle, the partial cowls can be rotated, to control the depth of the burr exposure and the resulting curvature of a planed bone surface.

DETAILED DESCRIPTION

Figure 1:
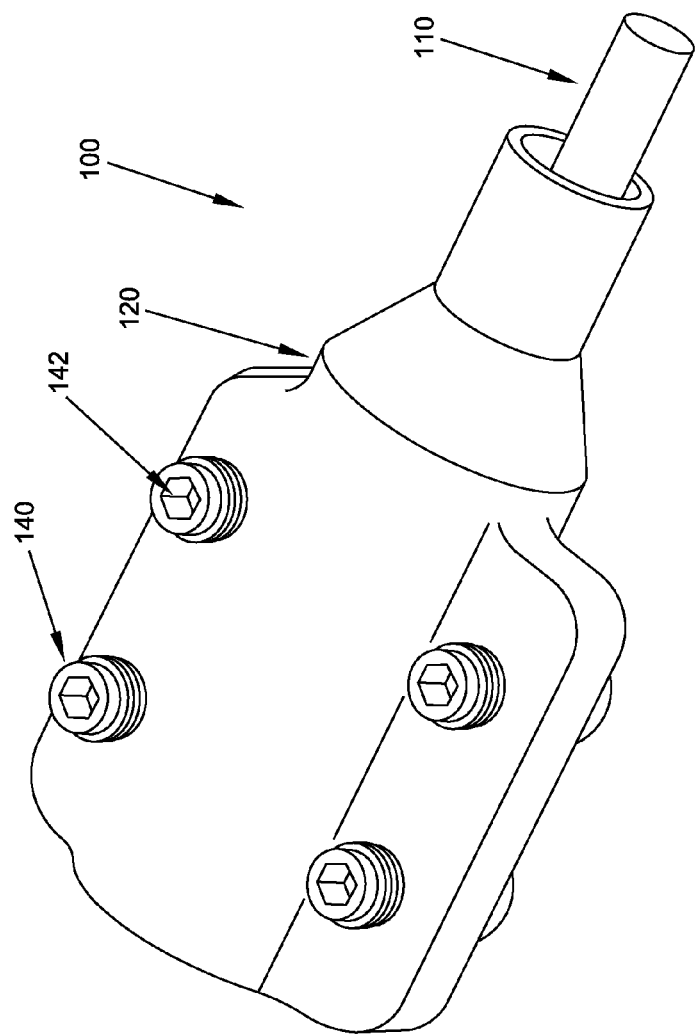
FIG. 1 is a perspective view of the "top side" of a planing tool with a rotatable shaft passing through an access tube. This tool has a cowl, and four threaded struts spaced around a grinding burr.

As summarized above, new types of surgical tools are disclosed, to support surgical procedures such as arthroscopic or other orthopedic preparation of bone surfaces, so that a prepared bone surface will be ready to securely support an implant.

To simplify the description and illustrations below, the discussion below and the figures herein describe tools that can be used to prepare flat or curved bone surfaces in an articulating joint (such as a knee, hip, shoulder, etc.). This can enable the bone surfaces to receive and securely support prosthetic implants that can replace or regenerate injured or diseased cartilage. However, that particular use is not intended to be limiting, and the tools described herein (including variants of such tools, modified in ways that will be apparent to those who are skilled in this type of tool design and/or use, after they have studied the teachings herein) can be used for other types of minimally-invasive surgery, such as spinal surgery, surgery to correct genetic malformations and/or bone-related diseases or injuries, surgery to implant other types of medical devices (such as devices for electrostimulation of muscles or nerves, devices for long-term drug release, devices that can sequester transplanted cells to prevent immune rejection, etc.), and surgery to reduce the sizes or modify the shapes of benign tumors or other unwanted growths.

Many of the tools disclosed herein are referred to as "planing" tools, or in some cases as shaving tools if they use a particular type of blade system known in the art. As described in the Background section, both of these types of tools are used to provide smooth surfaces (which can be rounded, curved, flat, etc.). Such tools are different and distinct from other types of tools, such as drills, routers, etc., which are used to create or modify holes, grooves, or other alterations in smooth surfaces. In general, planing tools with abrasive or grinding burrs are normally used to prepare smooth hard surfaces on bones, while shaving tools with sharp blades rather than burrs are used to prepare smooth and even surfaces on soft tissues. Most such burrs and blades use high-speed rotation; however, reciprocating or other motion could be used, if desired, in at least some cases.

To organize and simplify the description below, the planing tools and devices described herein are divided under several subheadings, with each subsection describing certain options and embodiments. Those subsections are sequenced as follows: (1) tools with grinding burrs mounted directly on the end of a rotating shaft, referred to as "direct" or "in-line" mounting; (2) tools with in-line mounting burrs, which also use external levers on a tool handle to enable a surgeon to open or close partial cowl components that partially surround a grinding burr, to adjust the depth of a burr and the curvature of a planed surface; (3) tools that use controllers (such as levers, on the handle) to control a set of pinchers or other manipulators (such as a cautery tip, suction tube, etc.) that will act in conjunction with a grinding burr or shaver blades, at the working end of a tool; and, (4) tools with grinding burrs having angled mountings that require drive-coupling mechanisms.

After those four subsections have been completed, an additional section describes several types of guidance-and-control devices and systems (such as templates, computer-controlled servo systems, etc.) that can be used in conjunction with these tools.

Planing Tools With "In-Line" (Direct-Mounted) Grinding Burrs

Figure 2:
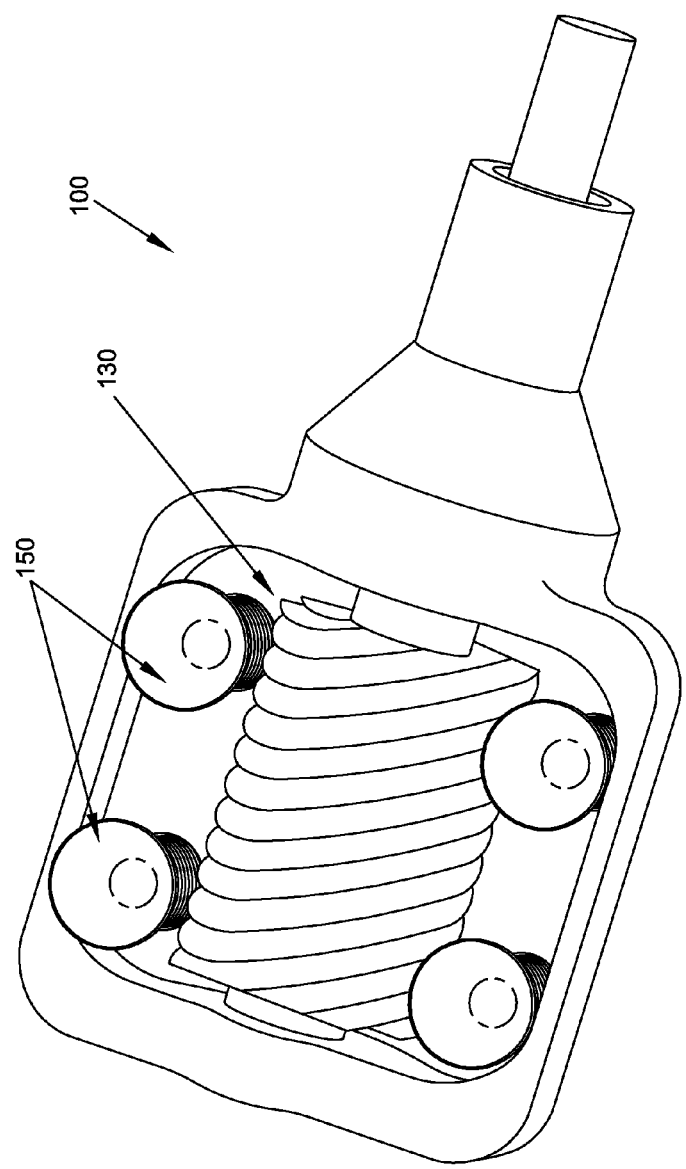
FIG. 2 is a perspective view of the "underside" surface of the same planing tool, showing the rotating burr, and the adjustable struts with smooth "feet" that will slide across a bone surface during an operation.

FIGS. 1 and 2 provide top and bottom perspective views of one embodiment of a planing tool 100. The main components and subassemblies of tool 100 include a rotating driveshaft 110, which enters a cowl 120, and which is affixed to a rotating burr 130 as shown in FIG. 2. This design provides simple but secure "in-line" or "end-mounted" fixation of a grinding burr 110 directly onto the end of a rotating shaft 120. Accordingly, this embodiment offers an uncluttered approach to describing various adjustment and control options that can be provided in any of several different cowl designs. Similar adjustment mechanisms can be used in planing tools with burrs that are angled in ways that require drive interfaces, as described below.

If desired, burr 130 can be fabricated as a part of the same piece of metal that forms the driveshaft 110. Alternately, if driveshaft 110 is hollow (to provide a suction pathway), burr 130 can be securely mounted at the end of driveshaft 110 by various means, such as welding, use of a noncircular driveshaft tip combined with a strong metal adhesive, etc. A threaded fitting also can be used, if rotation will occur only in one direction during use; this is a preferred operating mode, since angled (helical) blades on a cylindrical burr can help pump blood and entrained debris out of the operating field, and into suction cannula 122.

Cannula 122 can be created by either or both of: (i) an open gap in cowl neck 124 around driveshaft 110, and/or (ii) a hollow rotating driveshaft 110, which can have an angled opening that will create pumping force when it spins rapidly.

Collars 124 and 125 (which also can be called bushings, washers, etc.) have smooth surfaces, and help prevent any vibration of burr 130. Cowl neck 124 is shown in truncated form; in a tool, it normally will provided by (or affixed to) the non-rotating sleeve that forms the elongated handle of a planing tool.

The sizes of the tools described herein need attention, since they must be miniaturized, to enable them to: (i) fit through an arthroscopic, laparoscopic, or similar insertion tube, which in most cases has roughly the diameter of a finger, and (ii) provide mobility and maneuverability, inside a joint or other body part. A complete cowl, including any lateral "wings" or extensions 129 which interact with adjustable struts 140, generally should be about ½ inch (about 1 cm) or less in width, and about 1 inch (about 2.5 cm) or less in length. Because tool 300, illustrated in FIGS. 4-8, does not require any such "wings" 129, it generally is preferred over the design of tool 100.

FIG. 1 depicts the upper ends of four threaded shafts 140, showing hexagonal sockets 144 which allow shafts 140 to be rotated, using a hex wrench or similar driver. Rotation of threaded shafts 140 will control the extension (or retraction) of feet 150, shown in FIG. 2. In ways that become clear from FIG. 21, extension or retraction of feet 150 can be used to generate any of several types of surfaces. If the feet are extended below the lowest point on the burr surface, the tool will create a planed surface in a convex area, such as on a femoral runner surface, or on the "ball" portion of a ball-and-socket joint. If the feet are at the same height as the burr surface, a flat and planar surface will result. If the feet are retracted to a height above the burr surface, a concave surface will result, such as in the socket portion of a ball-and-socket joint.

In most situations, it will only take a few seconds for a surgeon to withdraw the tool head from a joint via the insertion tube, adjust the feet to any desired height, and return the tool into the joint. Nevertheless, an electromechanical, hydraulic, or other system can be developed if desired, which can allow a surgeon to rotate any or all of shafts 142 from outside a joint, to adjust their heights while an operation proceeds without interruption.

In another alternative embodiment, a fixed and non-adjustable cowl edge can be used as the bone-contacting component on one side of the burr, while a height-adjustable mechanism (s) is placed on the other side of the burr. Since only one mechanism on one side of the burr will need to be adjusted, this can simplify the design of an electromechanical, hydraulic, or other system that will allow a surgeon to adjust the height of the burr (and the curvature of a planed surface), from outside a joint, while the tool remains inside the joint.

In another preferred alternative, described in more detail in the next subsection below, adjustable shafts 140 and feet 150 can be replaced by a different type of mechanism that allows one or possibly two exposed and accessible levers, mounted on the tool handle, to control the rotation of partial cowl components at the working end of a tool.

For completeness, FIG. 3 is a side view of a different type of planing tool 200 with an in-line grinding burr 230 mounted directly on the end of a rotating shaft 210, with cowl 220. FIG. 3 illustrates adjustable shafts 240 with smooth-surfaced feet 242, with a "stepper" adjustment mechanism 244 rather than threaded shafts.

Accordingly, when restated in language suited for patent claims, the essential components of this type of surgical tool include: (a) a handle, with means for coupling said handle to a drive unit that can provide rotational power and suction to said surgical tool; (b) a cowl assembly affixed to one end of said handle, wherein said cowl assembly has at least one component designed to contact and move across a bone surface during a planing operation; (c) a movable burr mounted within said cowl assembly, having a first exposed surface region that will contact a bone surface during a planing operation, and a second surface region covered by said cowl; and, (d) means for moving (presumably rotating) said burr within said cowl. Various other options include suction capability, adjustable bone-contacting components that can be moved relative to a burr, etc.

In-Line Tools with Handle Levers that Rotate Partial Cowls

A mechanism mentioned above, which can enable a surgeon to alter and control the shape and curvature of planing surface without having to withdraw a tool to adjust it during an operation, is illustrated by planing tool 300, illustrated in FIGS. 4-7. The working end 302 of tool 300 is shown, in a partial cutaway view, in FIGS. 4A and 4B (with and without grinding burr 322). Working end 302 comprises: (1) a non-rotating outer sleeve 310; (2) driveshaft 320 with grinding burr 322 at its end; (3) a first partial cowl 330, which can be rotated relative to outer sleeve 310; and, (4) a second partial cowl 340, which also can be rotated relative to outer sleeve 310. The two partial cowls 330 and 340 will be at the ends of hollow concentric shafts, which will be positioned between outer sleeve 310 and driveshaft 320. FIGS. 4A and 4B also show: (i) rounded sleeve edges 314, which are part of outer sleeve 310; and, (ii) sleeve cap 316, which is affixed to sleeve edges 314, and which has a center post 318 to help stabilize rotating burr 322.

Figure 7:
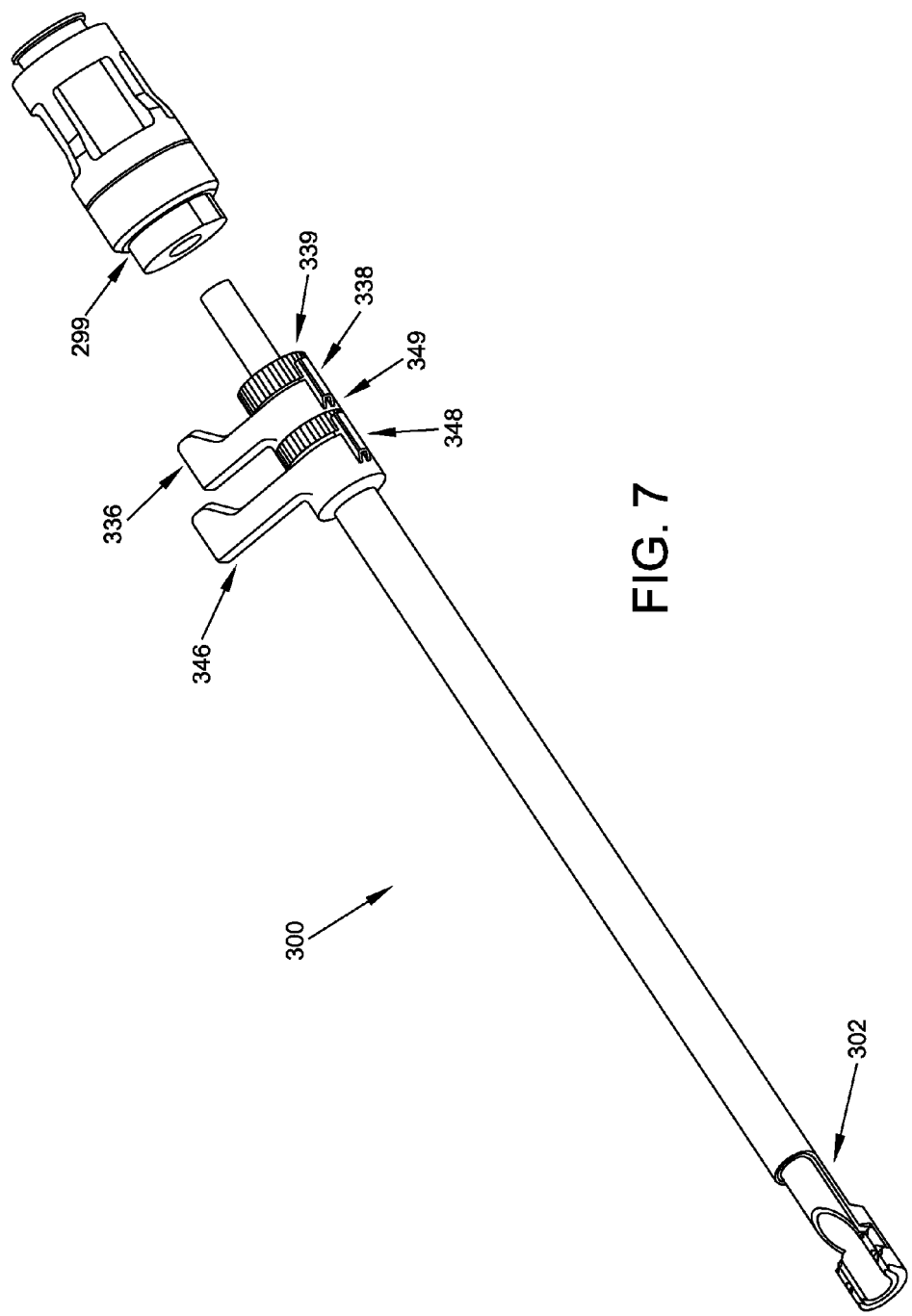
FIG. 7 is a perspective view of the working tip (without the burr), shaft, and handle of a tool, which has two movable levers that control the rotatable partial cowls at the working end of the tool.
Figure 8:
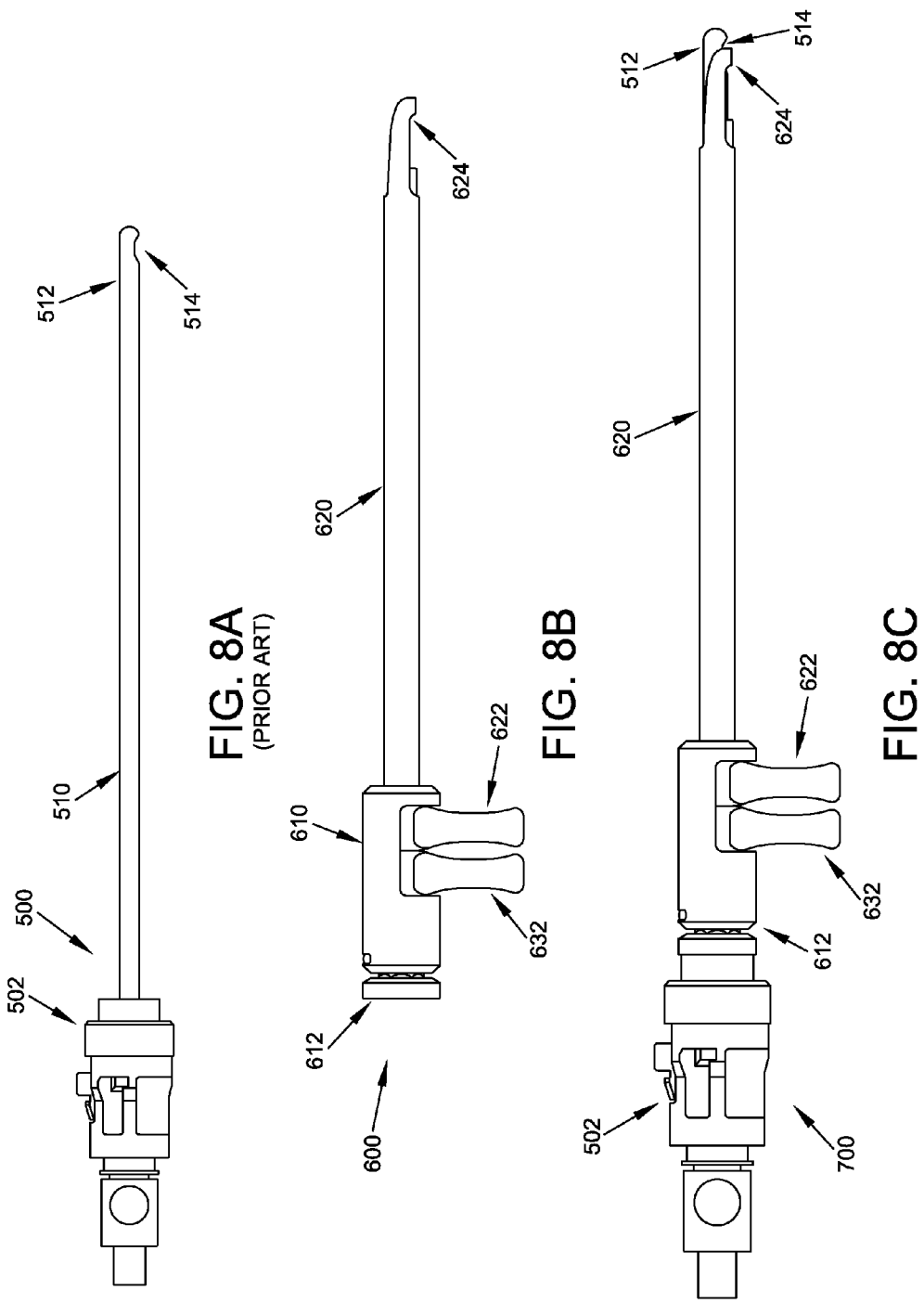
FIG. 8 indicates how a prior art shaving tool (FIG. 8A) can be fitted with a rotatable pincher assembly (FIG. 8B) to create a modified shaver tool with extendible pinchers.

The "arc tips" 334 and 344, at the working ends of partial cowls 330 and 340, comprise rounded and non-abrasive edges which can be rotated through a range of positions, from "wide open" to "fully closed". This movement is under the control of levers 336 and 346, mounted near handle end 304 of tool 300 as shown in FIGS. 7 and 8. Handle end 304 is designed to be coupled to a conventional drive unit mounting interface 299, at the end of a flexible cable that emerges from the drive unit.

The variable-sized opening that will be created in working end 302, when levers 336 and 346 are operated to rotate either or both sets of arc tips 334 and 344, can be referred to as a slot, aperture, window, exposed surface, or similar terms. This variable opening is indicated by callout number 361 in FIGS. 5A and 5B (which show a single opening size from two different angles), and callout number 363 in FIGS. 6A and 6B (which show a different opening size from two different angles). FIGS. 5A through 6B are cutaway views, with sleeve cap 316 removed so that the positioning of movable arc tips 334 and 344, relative to burr 322, can be seen in different positions.

Since both sets of "arc tips" 334 and 344 are concentric and cylindrical, and since both sets of arc tips surround burr 322, the width of the opening, between the first set of arc tips 334 and the second set of arc tips 344, at any particular moment or stage during surgery, will govern the depth to which grinding burr 322 can penetrate into a bone or other tissue surface, at that time during surgery.

Figure 5A:
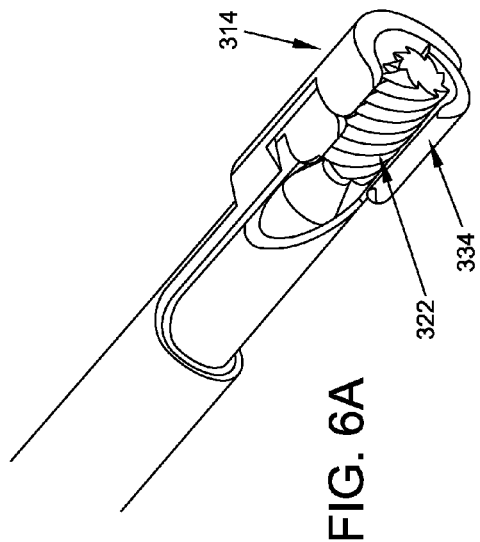
FIGS. 5 and 6 depict additional views of rotatable partial cowls at the working end of a tool, indicating how they can control the exposure and depth of a burr, relative to the cowl edges.
Figure 5B:
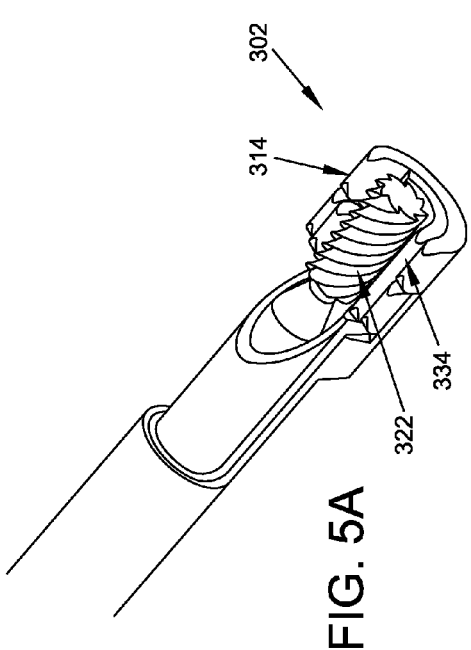

FIGS. 5A and 5B depict a "wide open" position. As can be seen more clearly in FIG. 5B, the lowest edge of grinding burr 322 extends well below the lowest edges of sleeve edges 314, first arc tips 334, and second arc tips 344. This "wide open" position allows "freestyle" use of the burr, by a surgeon.

Figure 6A:
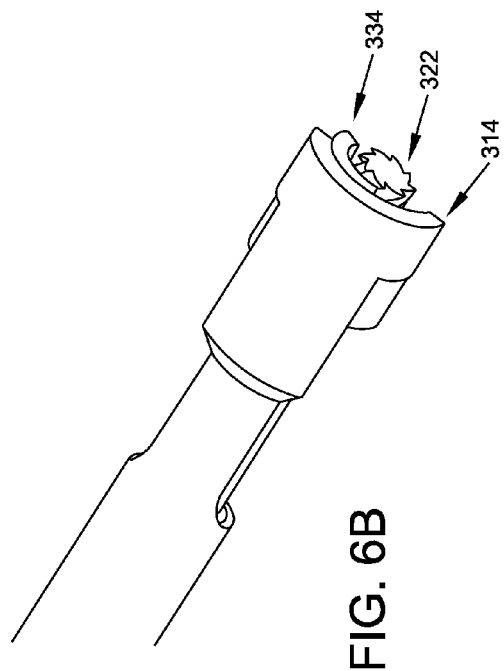
Figure 6B:
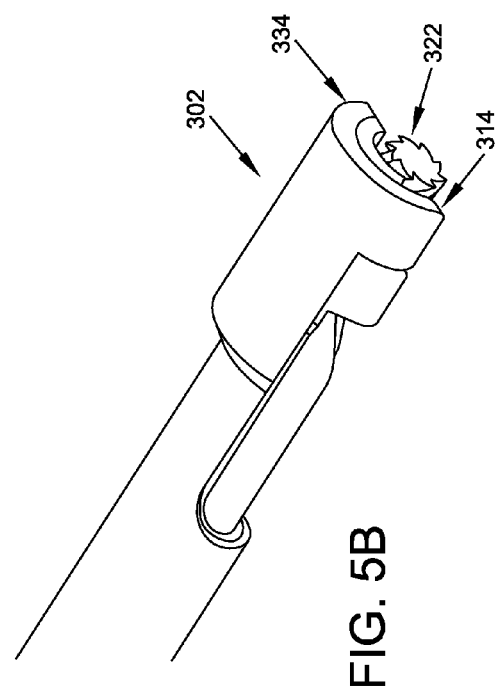

FIGS. 6A and 6B indicate that either or both of the partial cowls 330 and/or 340 have been rotated, to a point where first arc tips 334 and second arc tips 344 are almost linearly aligned with the lowest edge of burr 322. In this configuration, grinding burr 322 will dig slightly into a bone surface, to create a concave surface. If the arc tips are extended farther, until they reach a straight-line alignment with the lowest edge of the grinding burr, the tool will create a flat surface; and, if the arc tips are extended still farther, the tool will create a convex surface.

Two points should be noted, regarding the use of levers or similar devices as the control mechanisms that are mounted on the handles of such tools. The first point is this: various different types of control mechanisms can be used, if desired. Scissor-type grips, as used in rotary basket punches, offer an example of a mechanism other than the types of levers illustrated in FIGS. 4-14. However, the use of levers that are mounted on axles that are concentric with, or at least parallel to, the main axis of a tool shaft, can provide an important advantage over most other systems, since a lever system can provide direct and immediate visual indication (and confirmation) of a manipulator component's angular positioning, at all times while the tool is in use. That type of visual confirmation becomes even more valuable when a position-locking mechanism is provided, such as shown by locking or detente devices 338, 339, 348, and 349 in FIG. 7, discussed below, since it can enable a surgeon to focus on various other aspects of an operation.

In an alternate preferred embodiment, a bone-contacting rounded edge on one side of the burr, shaver, or other device can be fixed and stationary (relative to the non-rotating outer sleeve of a tool handle), and a single lever-controlled movable partial cowl can be provided on the other side of the burr, shaver, or other tool. This can simplify the design and manufacture of various types of single-level tools, compared to the two-lever tools shown in FIGS. 4-14.

FIG. 7 is a perspective view of tool 300, with a partial cutaway shown at working end 302, and without driveshaft 320 or grinding burr 322 present. This view shows levers 336 and 346, which are affixed to the handle ends of partial cowls 330 and 340. Lever 336 has a detente or locking device 338, having a wedge-shaped interior edge that will engage a series of ridges, around knob or sleeve 339. This detente or locking system will hold lever 336 at a specific angle set by the surgeon, until the surgeon chooses to rotate lever 336 (and partial cowl 330) into a new position. Similarly, lever 346 has a detente or locking device 348 that will engage the ridges around knob or sleeve 349. FIG. 7 also depicts a conventional drive unit interface 299.

Tools with Accessory Devices that can be Rotated, Extended, and Retracted

After the rotatable partial cowl system shown in FIGS. 4-7 was developed, it was recognized by the Applicant that this approach could be modified and expanded into additional areas, to create a new class of surgical tools having certain types of "accessory" components that can make such tools much more useful in a wide variety of surgical procedures.

This work initially grew out of the realization that a rotatable partial cowl system as described above could be modified and adapted, in a way that would effectively convert two partial cowl components, into two pincher or plier components, which could work together to grip a piece of soft tissue between the tips of the pinchers. While a set of pincher or plier tips would not be especially useful in a planing tool that uses a grinding burr to plane a hard bone surface, a pincher or plier system would be useful, if it is adapted to be added to certain other types of devices, such as certain types of "shaving tools" used in minimally-invasive surgery.

After realizing that rotatable pincher or plier components could be developed in a manner that would allow them to be added to an existing tool such as a shaver, the Applicant realized that such accessory-type components could be even more useful, if they could be designed in a way that would allow one or more accessory components to be extended beyond the normal tip of a tool, when desired, under the control of a surgeon. For example, if two pincher tips mounted at the end of a shaving tool can be extended while in an open position, rotated into a closed gripping position, and then retracted, whenever desired by a surgeon, this can allow a surgeon to effectively reach out, grip a piece of soft tissue, and pull that tissue into the cutting portion of the shaving tool.

After recognizing that concept, the Applicant then realized that if a cautery electrode, a suction tube, a flexible finger-like guiding device, or various other "accessory"-type devices could be mounted at the ends of various types of conventional minimally-invasive tools, in a way that would allow the accessory component to be extended beyond the normal tip of the tool when desired by a surgeon, and then retracted when desired by the surgeon, that could add useful additional functions and capabilities to a variety of surgical tools used in numerous types of surgeries.

Accordingly, the Applicant set out to develop a design for add-on accessory-type components that can be mounted onto existing tools, in a manner that will allow one or more accessory components to be extended beyond the normal working tip of a tool. His efforts were successful, and such a design is illustrated in FIGS. 8B through 14.

FIG. 8A shows a conventional tool 500 known in the prior art, usually called an arthroscopic (or laparoscopic, etc.) shaving tool, or shaver. At one end is a handle or base 502, which can be coupled to a flexible cable that emerges from a conventional drive unit, such as sold by Smith & Nephew, or Stryker. A long and hollow non-rotating outer shaft (or sleeve) 510 is provided, with a "working end" 512. Working end 512 has an orifice 514, usually in the shape of an oval, with razor-sharp edges surrounding the orifice. Inside the non-rotating outer shaft or sleeve 510 is a second hollow shaft 520 (partially shown in FIG. 9A), which spins rapidly during use. Inner shaft 520 also has an oval-shaped orifice 522, with sharp edges surrounding it.

The two orifices 514 and 522, in outer shaft 510 and inner shaft 520, are aligned with each other, as shown in FIGS. 9A and 10A. When the tool is in use, and when orifice 514 is pressed against soft tissue, any tissue that bulges or otherwise protrudes into orifice 514 is sheared off, by the leading sharp edge of the spinning internal orifice 522. The hollow inner shaft 520 acts as a suction cannula; it suctions blood and entrained solids out of the operating field and into handle or base 502, which has an outlet port that carries the liquids and solids to a collection device.

As mentioned above, shaver tool 500, in FIG. 8A, is prior art. The new device 600, referred to herein as pincher assembly 600, is illustrated in FIG. 8B. When pincher assembly 600 is fitted onto and affixed to shaver tool 500, the resulting combined tool 700, shown in FIG. 8C, is provided with additional features and capabilities.

Pincher assembly 600 has several subassemblies, illustrated in FIGS. 8B through 14. Briefly, it comprises: (i) a base or handle assembly 610, a portion of which can be slidably extended or retracted as described below; (ii) an outer hollow shaft 620 (shown in FIGS. 12 and 13) with a control lever 622 at the base end, and a first pincher component 624 at the opposed working end; and, (iii) an inner hollow shaft 630 (also shown in FIGS. 12 and 13) with a control lever 632 at the base end, and a second pincher component 634 at the working end.

Figure 9:
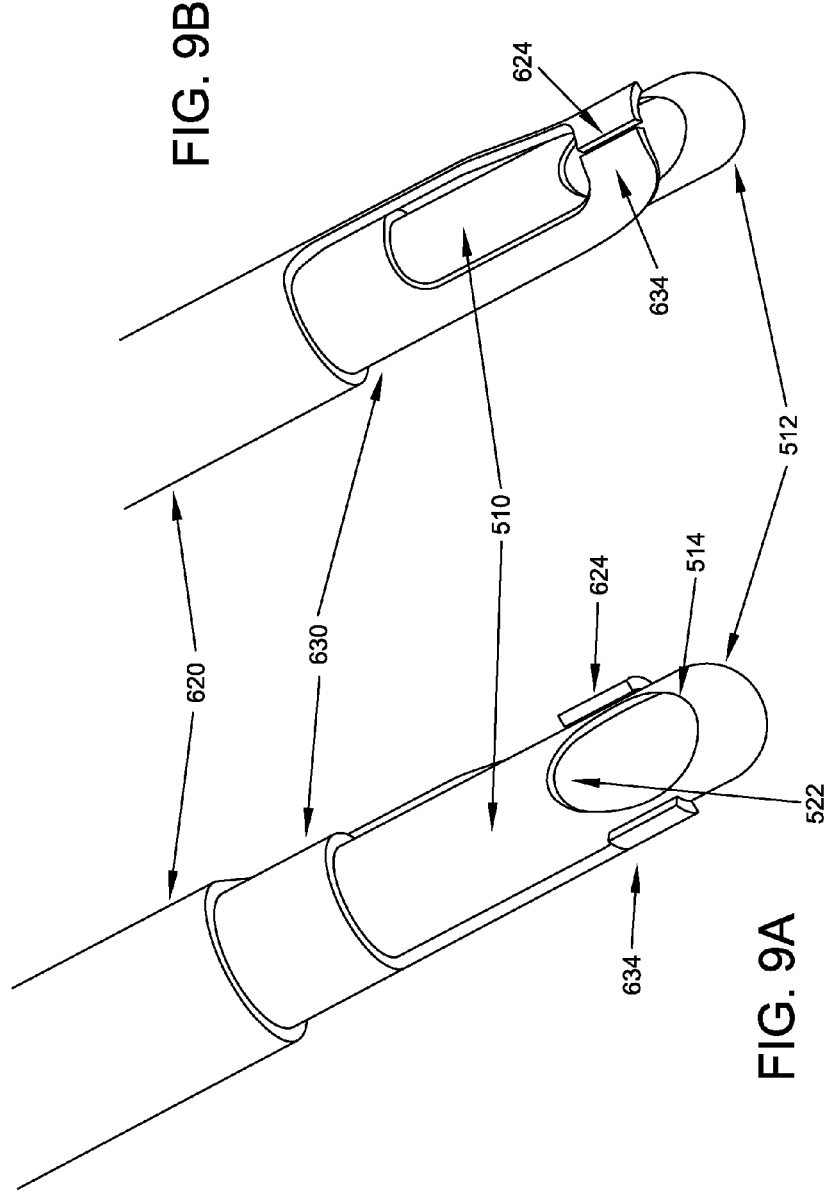
FIG. 9 shows how rotatable pinchers can be opened and closed, over a shaving tool orifice with a fixed outer blade and a spinning inner blade.
Figure 10:
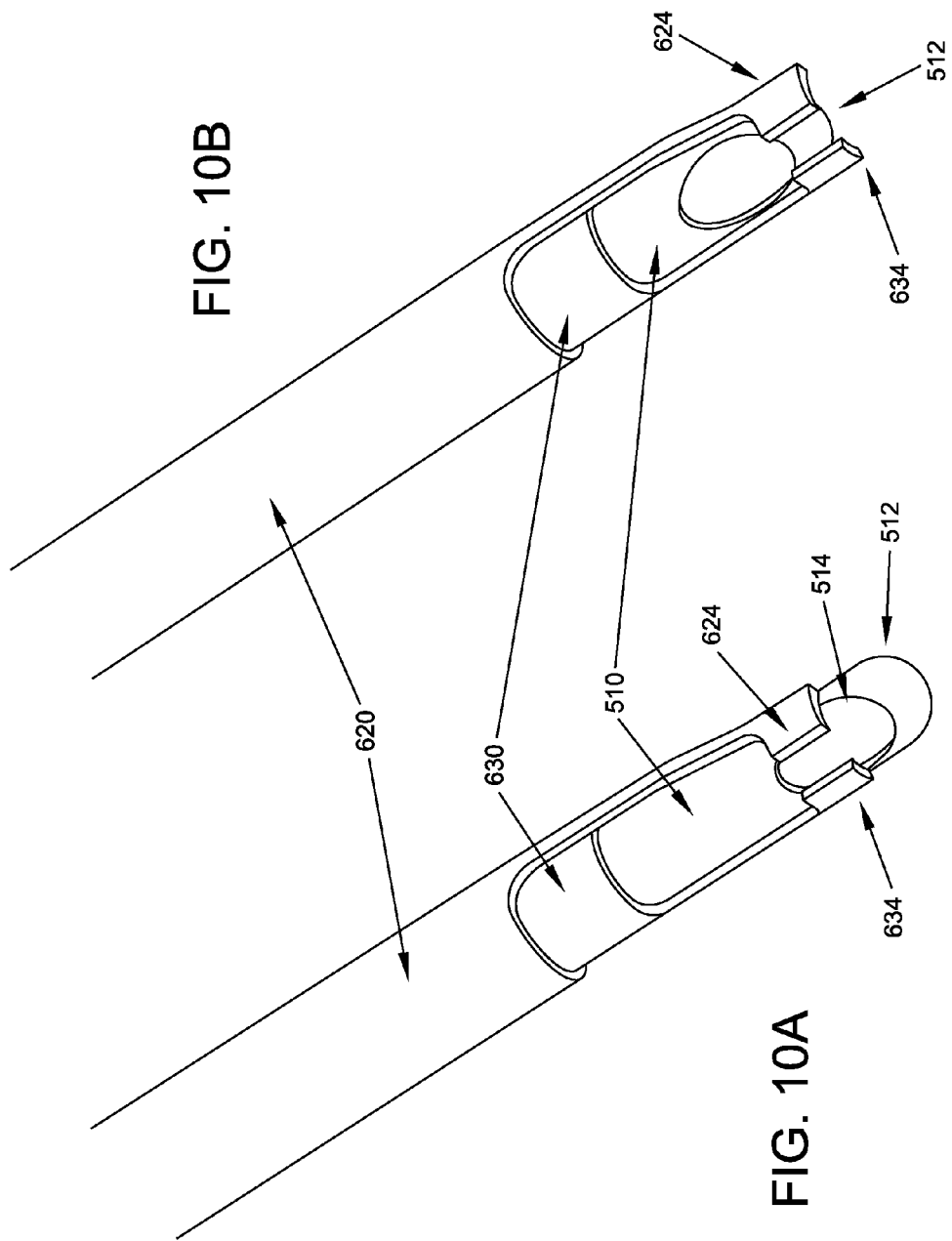
FIG. 10 shows how rotatable pinchers also can be extended, linearly, beyond the normal working end of a shaving tool.
Figure 11:
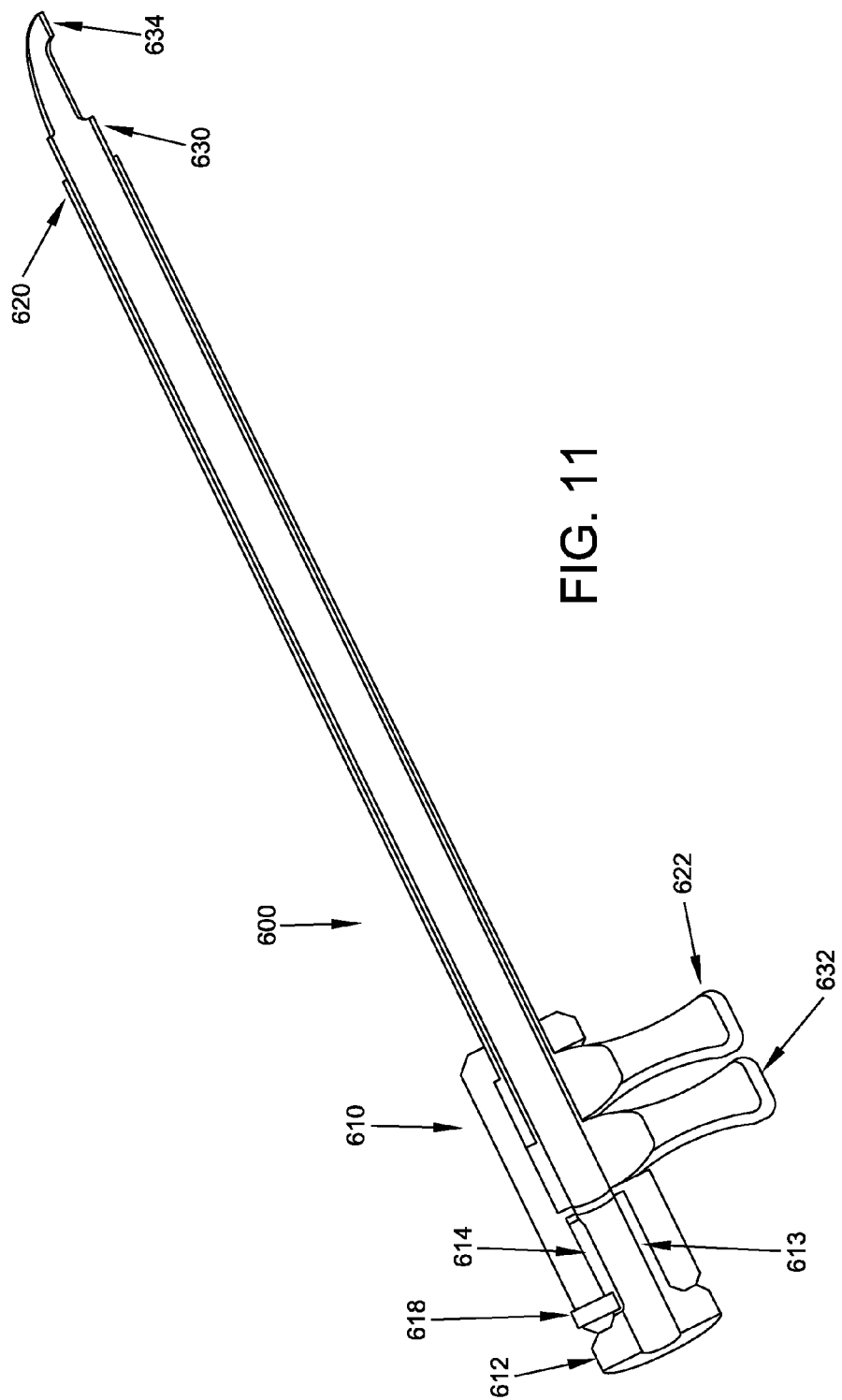
FIG. 11 is a cutaway view, depicting a movable carriage that uses a pin-in-slot assembly, to enable linear extension and retraction of a pincher assembly that can be retrofitted onto a shaving tool.
Figure 12:
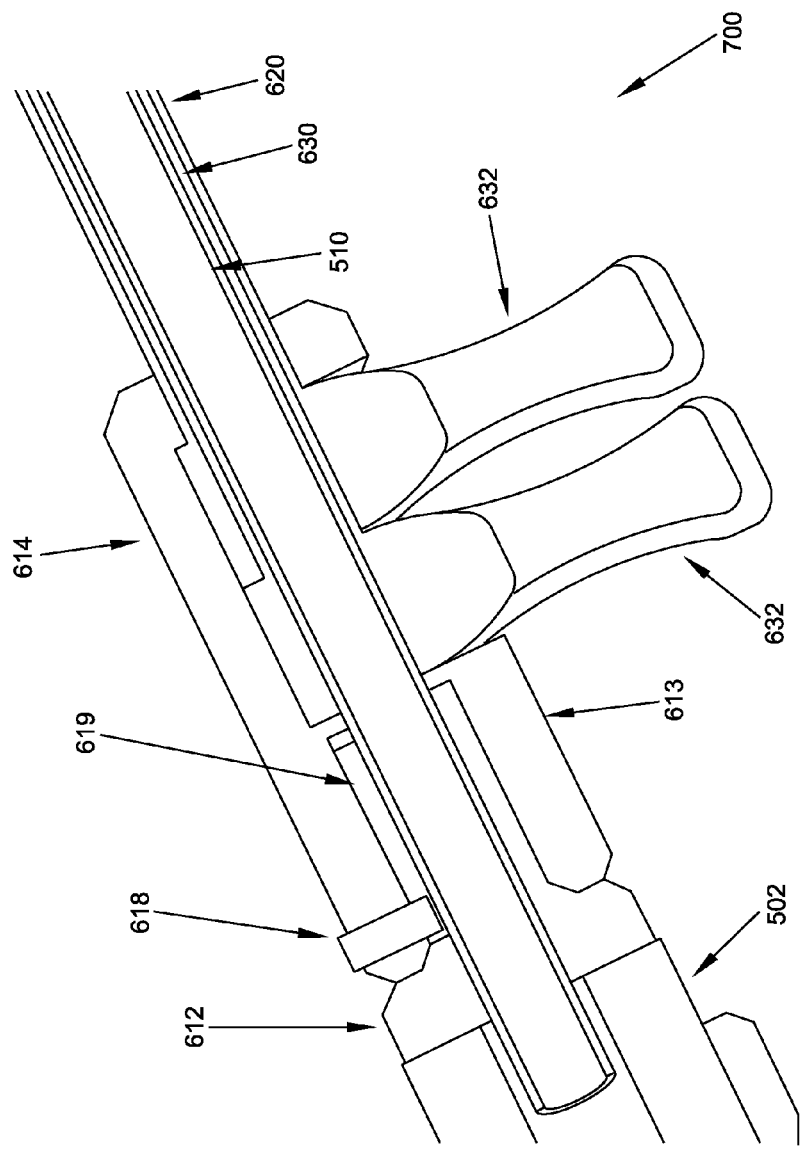
FIG. 12 is a closer view of the carriage assembly in a retracted position, pressed against a collar component of the pincher device.
Figure 13:
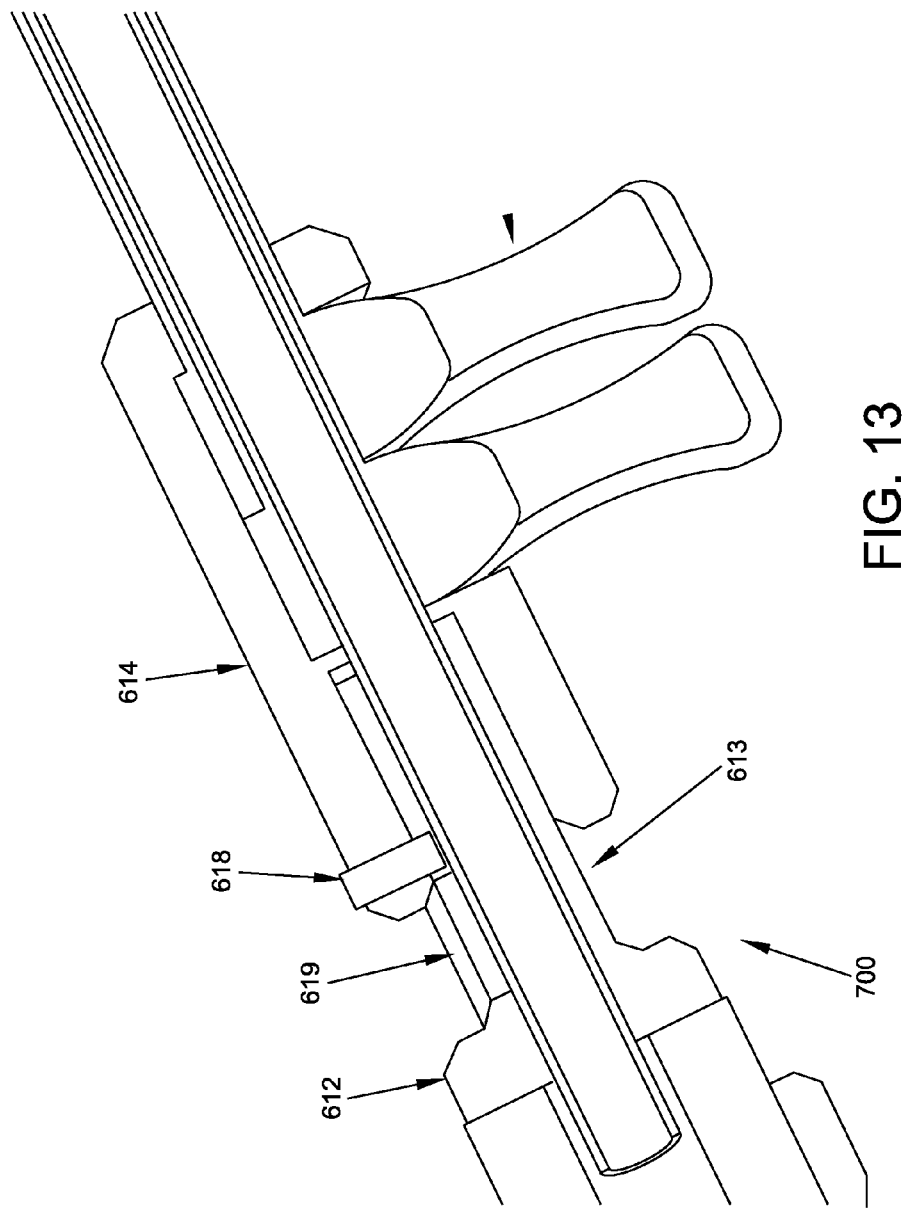
FIG. 13 is a close view of the carriage assembly in an extended position, near the end of a short non-circular shaft provided by the collar component, with a pin mounted in the carriage moved to the end of a constraining slot in the collar shaft.

When pincher assembly 600 is mounted on and affixed to shaver tool 500 (secure affixation can use an adhesive, a set screw, or other suitable means), the working end 512 becomes a modified and combined system as shown in FIGS. 9A through 10B. In FIG. 9A, the outer shaver shaft 510 with its orifice 514 is shown, and one of the edges of the inner shaft orifice 522 is also visible, along the edge of orifice 514. The two pincher sleeves 620 and 630 are shown, surrounding the shaver shaft 510. In FIG. 9A, pincher tips 624 and 634 are in an open position, while in FIG. 9B, pincher tips 624 and 634 are closed together. Rotational (opening and closing) motions of the pincher tips 624 and 632 are under the control of levers 622 and 632, shown in FIGS. 11-14. Each lever is affixed to a hollow cylindrical sleeve. As shown in FIGS. 11-13, lever 632 rotates inner sleeve 630, which moves pincher tip 634, while lever 622 rotates outer sleeve 620, which moves pincher tip 624.

FIG. 10A shows pincher tips 624 and 634 in a retracted position, directly over orifice 514, while FIG. 10B shows pincher tips 624 and 634 in a partially extended position, beyond orifice 514, in a manner that will enable the pinchers to grip soft tissue and pull it to the orifice. The sliding motions that enable such extension and retraction of pincher tips 624 and 634 are enabled by a sliding but non-rotating mechanism shown in FIGS. 11-14.

Figure 14:
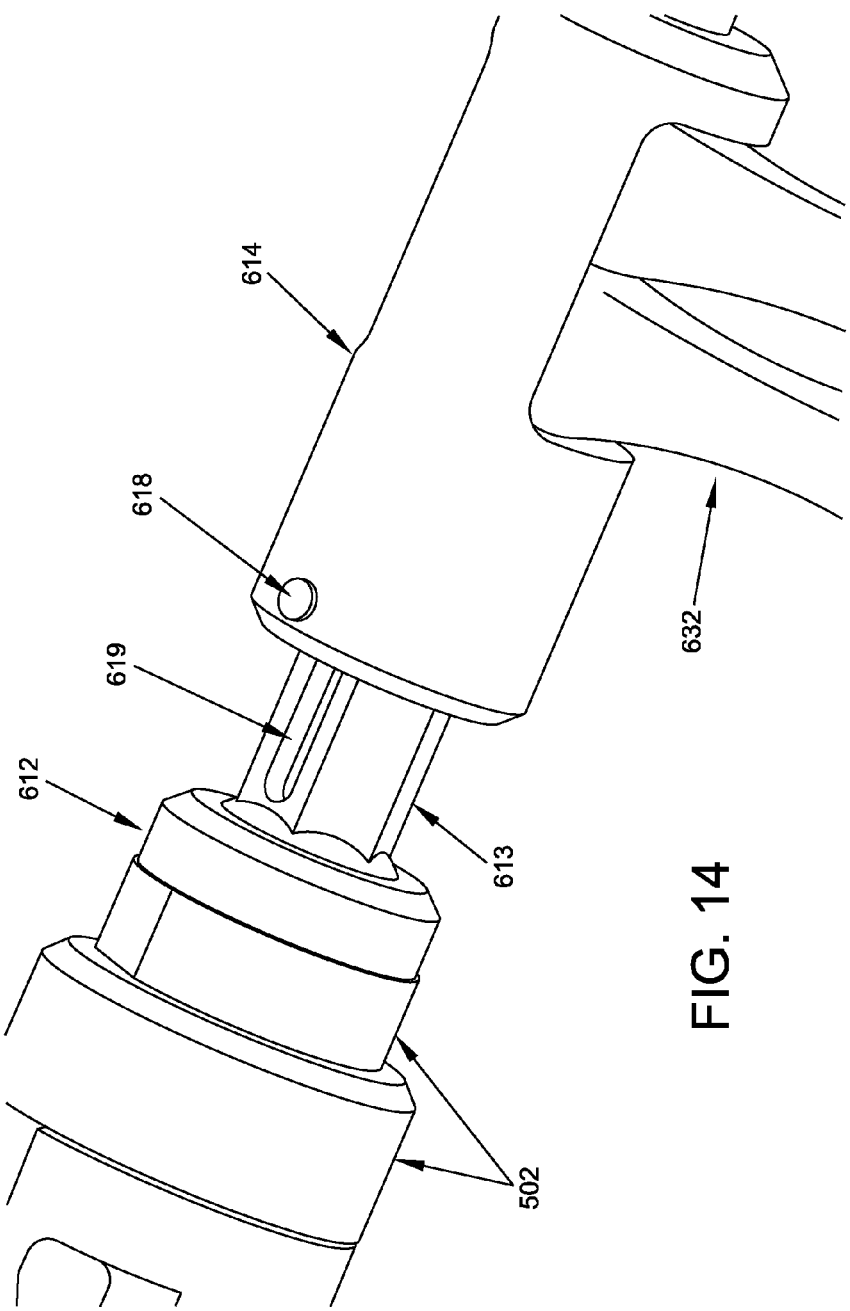
FIG. 14 is a perspective view of the carriage assembly and collar component, showing the constraining slot in the non-circular shaft provided by the collar component.

Both of the two levers 622 and 632 are constrained within a movable "carriage" component 614, which is part of the base or handle assembly 610. The other main component of the base or handle assembly 610 is referred to as collar 612 (it can also be referred to as a root, or similar terms). As illustrated in FIGS. 12-14, collar component 612 includes and provides a short shaft 613, which is illustrated as having a hexagonal cross-sectional shape (a square, rectangular, or other non-round shape could alternately be used). Carriage component 614 has a center channel with an accommodating shape, which will allow it to slide a limited distance along the short shaft 613, in a manner that enables extension and retraction motions, as illustrated in FIGS. FIGS. 12 (which shows movable carriage 614 in a retracted position, nestled against collar 612) and 13 (which shows carriage 614 in an extended position, away from collar 612). A stop or detente mechanism should be provided, such as pin 618 (affixed to the carriage 614), which slides within slot 619 (which is molded or machined into short shaft 613, which is part of collar 612).

Accordingly, the complete pincher assembly 600 has been designed in a manner that enables controlled rotational motion (which enables opening and closing of the pincher tips), as well as controlled linear motion (which enables extension and retraction of the pincher tips). This can render such a pincher system very useful in numerous types of surgery.

That same type of design can also be adapted to provide various other types of highly useful accessory-type devices that can be added to existing tools, in ways that will allow one or more accessory components to be extended beyond the normal working tip of a tool, whenever desired, under the control of a surgeon. For example, if a cautery or coagulation electrode (such as, for example, a standard type of cautery electrode known as a "Bovie" among surgeons) can be provided as part of a surgical tool, mounted and operated in a way that allows the electrode to be extended slightly beyond the working tip of the tool when desired, and then retracted after cautery is finished so that the electrode will not be in the way of the main tool device, that could be very useful to surgeons, in quite a few settings. Similarly, if the tip of a suction tube could be temporarily extended beyond the normal working tip of a tool, and then retracted again so that it will not be in the way of the main tool device, that also could be very useful to surgeons, in quite a few settings.

Similarly, this type of system can be adapted to provide a finger-like extendible and rotatable projection, at the working end of a tool. This type of finger-like protrusion, which can be rotated in either direction and extended or retracted whenever desired, can be useful for various purposes, such as (i) moving soft tissue out of the pathway of a tool, or (ii) moving soft tissue into the pathway of a tool. If desired, this type of single-protrusion system also can be developed into a more complex system that can provide additional functions. For example, if a thin wire is embedded within or coupled to a flexible and pliable finger-like device, and if the wire is affixed to a point near the tip of the finger-like device, retraction of the wire can be used to bend the tip of the device in a desired direction, to create a hook-like structure.

Therefore, this type of system, which initially grew out of Applicant's efforts to develop specialized tools for repairing cartilage in articulating joints, can be adapted to various other types of surgical tools, to provide increased and improved functionality in numerous types of surgery.

When described in terms suited for a patent claim, this type of tool comprises: (a) a shaft assembly, having a shaft which establishes a dominant axis, a handle end, and a working end; (b) at least one control component affixed to the handle of the shaft assembly; (c) a nonextendible manipulator component (such as a burr, a set of blades, or a suction tube) at the working end of the tool, which cannot be moved in a linear manner relative to the shaft, and, (d) an extendible manipulator component mounted at the working end of the tool, which can be linearly extended, beyond the nonextendible manipulator component, by a surgeon operating a control device.

Tools with Angled Grinding Burrs and Coupling Interfaces

This subsection focuses on tools in which the axle of the grinding burr is angled, with respect to the shaft of the tool, in a manner that requires a drive-coupling interface. In most cases, the burr will be perpendicular to the tool shaft; however, acute or obtuse angled tools also can be created if desired.

It should be noted that, by using specialized flexible materials and designs to create non-rotating sleeves that enclose rotating driveshafts, tools can be (and have been) developed that can have a substantial degree of flexibility, near their working ends. Such materials and designs can enable the working ends of such tools to reach angles of roughly 10 or even 20 degrees. Furthermore, means can be provided, in at least some cases, to reduce the risk that the tip of a tool (and the outermost end of a cylindrical grinding burr) will exert more pressure, against a bone surface or other tissue, than the other portions of the grinding burr. As one example, a thin wire can be affixed to the tip of a tool, and to a fixation point an inch or so back from the tip of the tool, on the "top" side of the tool shaft. When the wire is retracted, it will cause bending and flexure of the working end of the tool.

However, since the nature and goal of a planing tool is to press a rapidly-rotating grinding burr or other cutting or abrasive surface against bone or other tissue, if a grinding burr is mounted at the end of a springy-type resilient flexible shaft, a serious risk arises that the result of a planing operation using such a tool will be to create an unwanted rippled, ridged, or other irregular surface, having a series of troughs (where the outermost end of a grinding burr dug too deeply into the bone or other tissue) alternating with crests (where other portions of the grinding burr passed over, without pressing with sufficient force against the bone or tissue). In most cases, a rippled, ridged, or other irregular surface is the opposite of what is desired from a planing operation, since that type of irregular surface cannot provide optimal support for a prosthetic implant.

Therefore, a need arises for at least some types of planing tools that will be provided with a "drive-coupling interface". That term is used herein to include a mechanical coupling system that will efficiently drive the rotation of a burr around an axle that is angled relative to the handle of the tool.

In one embodiment of such a tool, planing tool 800 (illustrated in FIGS. 15-17) uses a rotating driveshaft 810 which passes through a cowl device 820 to drive the rotation of a cylindrical burr 830. For convenience, FIG. 15 is deemed to be a "top" view, while FIG. 16 is deemed to be a "bottom" view; these directional terms presume that a planing tool will travel across the top surface of a predominantly horizontal bone surface, with the exposed (grinding) surface of the burr positioned on the bottom (lower) side of the tool, and with the cowl positioned on the top (upper) side of the tool.

Driveshaft 810 (truncated in FIGS. 15-17) passes through an access and suction tube 812 (also truncated). During a typical arthroscopic operation, clear saline solution is pumped through a tube, via an outlet positioned adjacent to a light source and miniaturized video camera. Continual emergence of a clear liquid from that tube (and passage of the liquid through the operating field, when the instruments are positioned and used properly) allows the surgeon to see the operating field more clearly, on a video monitor. Accordingly, tool 800 is equipped to provide suction for the clear liquid that is being continuously pumped through the operating field. That liquid will entrain and remove most of the cartilage flakes, bone chips, and other particles and debris that are created by the tool.

Figure 15:
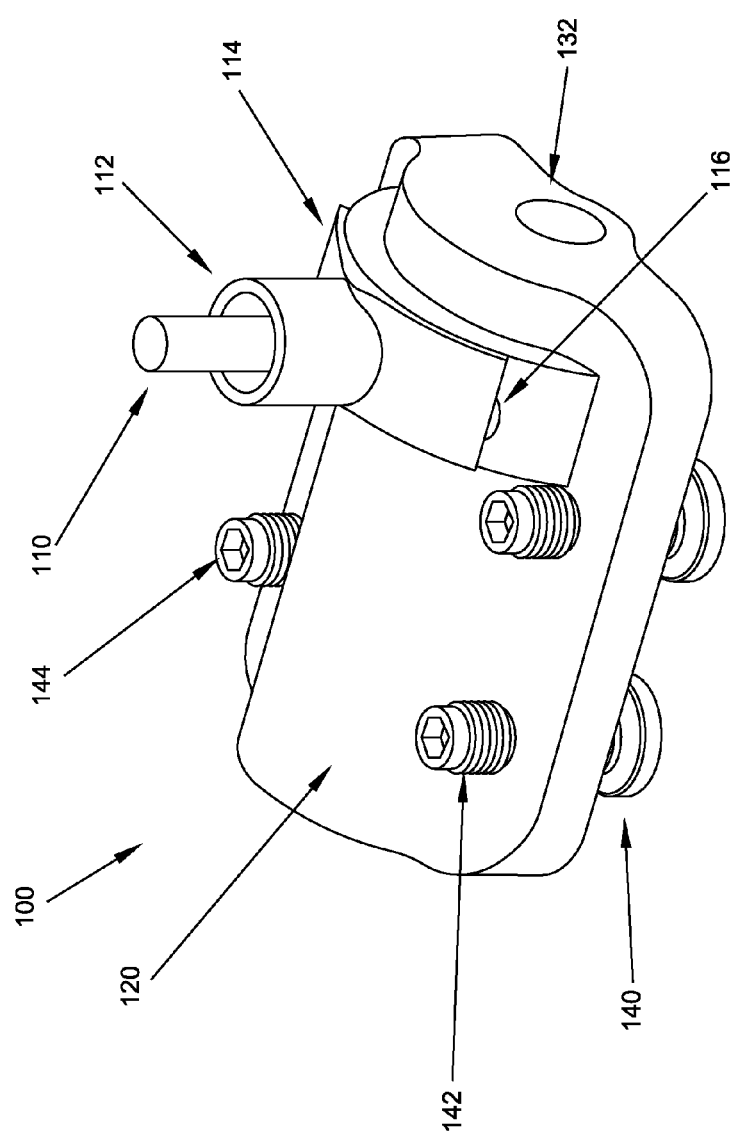
FIG. 15 is a perspective top view of a different type of planing tool, with a grinding burr mounted perpendicular to a rotating driveshaft that passes through the tool handle, and having a cowl access tube that can move in an arc across the top surface of the cowl.
Figure 16:
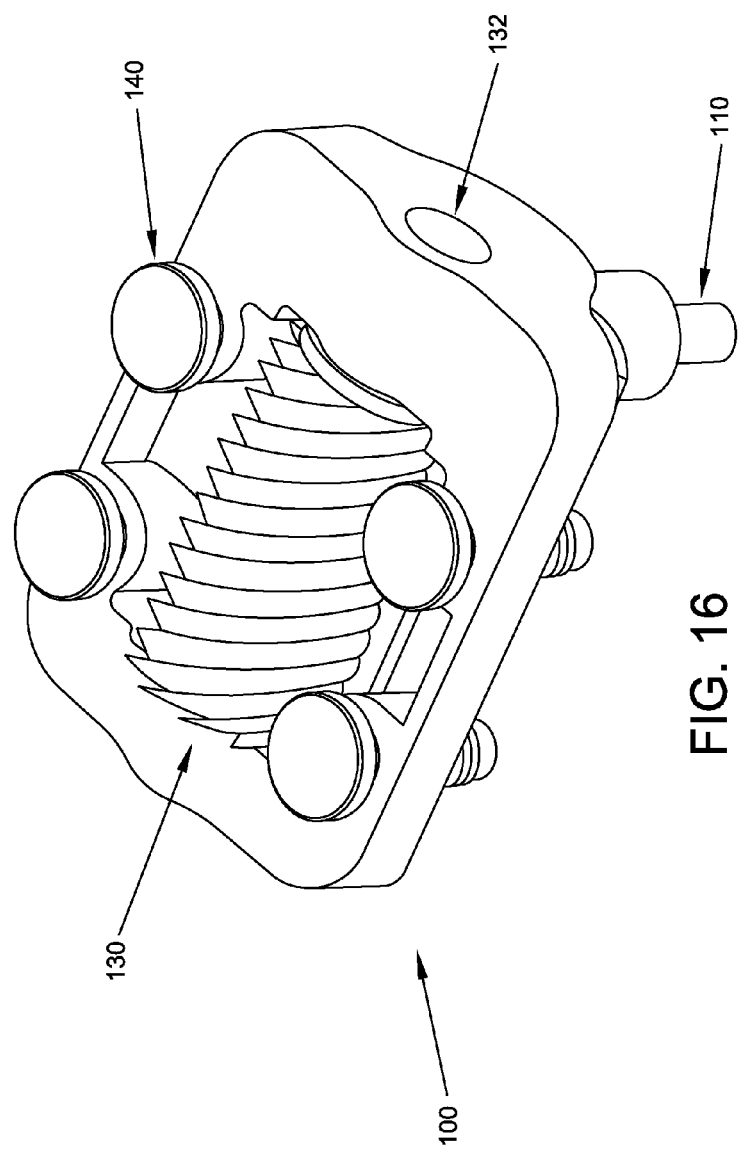
FIG. 16 is a perspective bottom view of the planing tool of FIG. 15.
Figure 17:
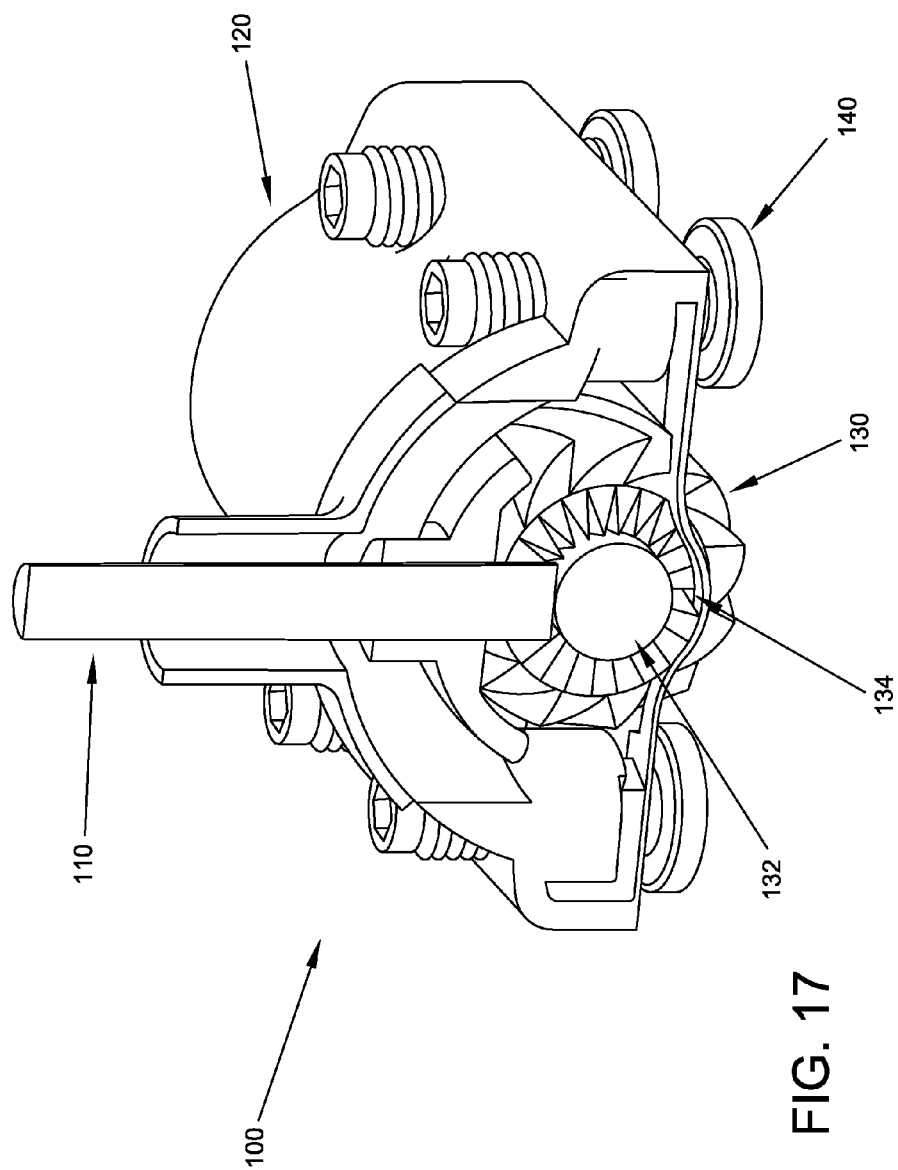
FIG. 17 is a cutaway end view, indicating how a gear surface at the end of the drive shaft can interact with a gear surface at the end of the burr cylinder, to drive rotation of the burr.

In the embodiment shown in FIGS. 15-17, access tube 812 is affixed to a curved plate 814, which will slide across the upper surface of cowl 820, traveling in a linear slot 816. This will allow a degree of control over the motion of the tool 800, since the handle end of access tube 812 will be accessible to the surgeon, outside the joint that is being repaired. If desired, the accessible end of access tube 812 can be coupled to any of various types of handles and/or mechanical or computer-coupled devices that can provide increased torque and/or precision. An alternate attachment and control mechanism, to allow the shaft/handle to interact with the cowl in a different manner that may provide better mechanical control over the motion and travel of the tool, is discussed below and illustrated in FIGS. 20 and 21.

FIG. 15 also depicts an exposed end of burr shaft 832, and three of the adjustable feet 840 that will ensure that the rotating burr 830 travels at an appropriate height, as it travels across a bone surface that is being prepared to receive an implant. Threaded shafts 842 (with hexagonal sockets 844, which can be rotated by a hex wrench) are illustrated, to indicate that extension of the feet 840, below the lower surface of cowl 820, can be adjusted. As mentioned above, an electromechanical or hydraulic system can be developed that will allow a surgeon to adjust the extension of the shafts 842 from outside a joint, while an operation continues without interruption (it also should be noted that such shafts can be provided with various adjustment mechanisms other than threaded exteriors, such as piston mechanisms, geared systems, linear electric motors, etc). An externally-controlled adjustment mechanism can help a surgeon more easily create the proper curvature for a bone surface that is being prepared, such as a femoral runner, which has a "cam" type curvature rather than an exactly round curvature.

Figure 21:
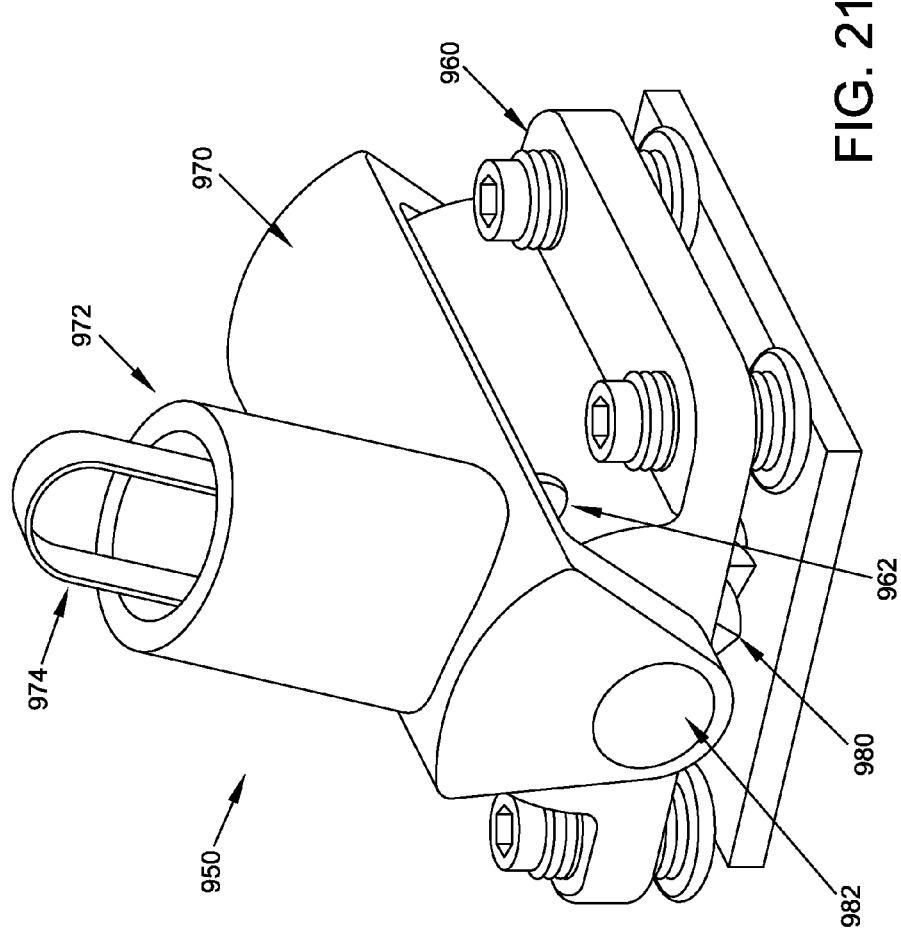
FIG. 21 is a side view of a planing tool, showing the "foot" components at a height that causes the burr to prepare a flat surface. If the feet are extended lower, the burr will create a planed convex surface, such as on a femoral runner.

FIG. 16 illustrates the "bottom" side of tool 800, with a clear view of grinding burr 830, which is mounted on shaft 832. If desired, a variety of burr surfaces can be provided, on interchangeable tool heads. For example, some burrs can be provided with rows of sharp cutting edges or teeth, for rapid removal of bone material, while others can be provided with sandpaper-like surfaces, for final preparation of smooth surfaces. This view shows all four of the smooth-surfaced "feet" 840, which can be adjusted in height to create a convex, concave, or flat surface, as indicated by FIG. 21.

FIG. 17 illustrates a cutaway view of one end of tool 800. This drawing illustrates how a gear surface at the end of rotating shaft 810 can impart rotation to the burr 830, via an accommodating radial-type geared surface 835 near the end of burr 830.

Figure 18:
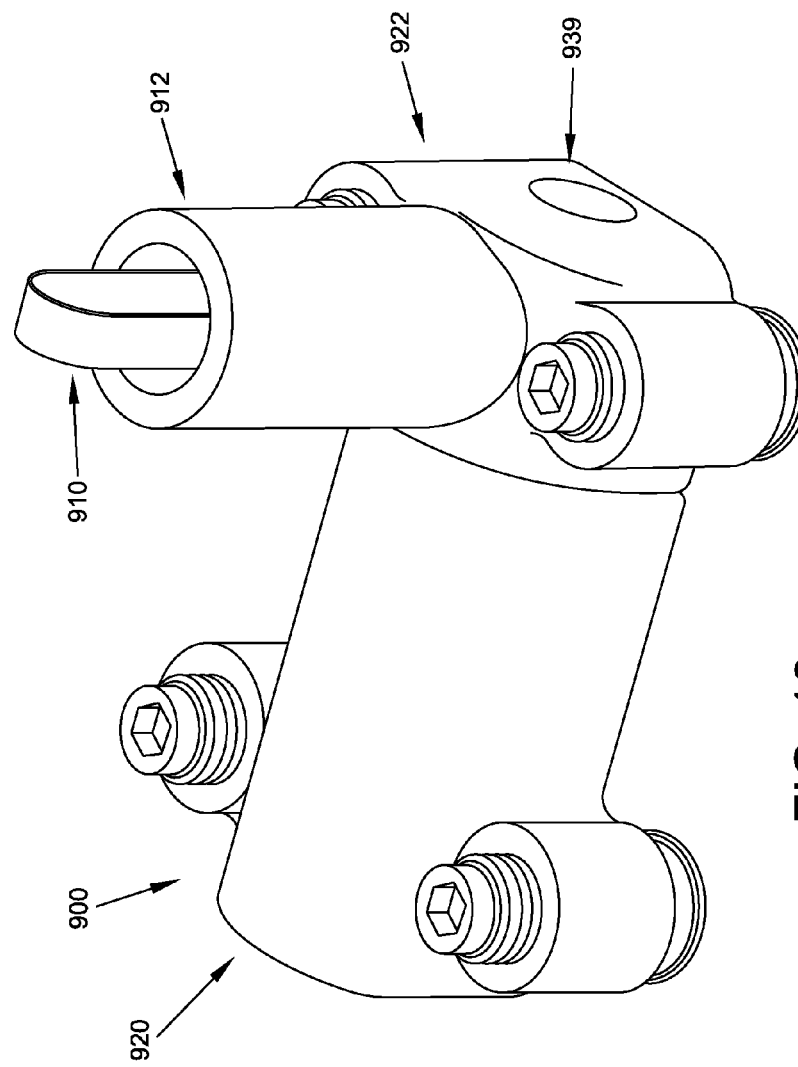
FIG. 18 depicts a different drive mechanism for a planing tool, using a flexible drive belt that passes through an access tube.
Figure 19:
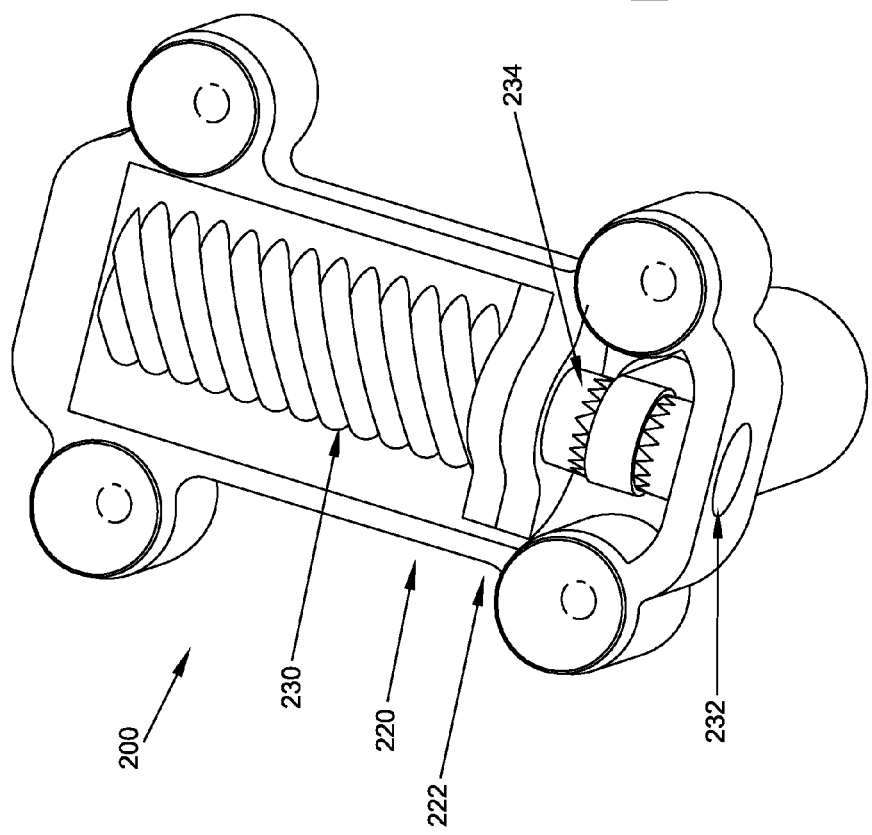
FIG. 19 is a perspective bottom view of the planing tool of FIG. 18, showing the drive belt passing (in tension) across a non-smooth surface of the burr shaft.

FIGS. 18 and 19 illustrate an alternate design for a tool 900, which uses a thin and flexible drive belt 910 to drive the rotation of grinding burr 930. This belt will be operated in tension, and it will drive rotation of burr 930 by encircling and pulling against a ridged, knurled, or other non-smooth surface segment 934 of burr shaft 932, as shown in FIG. 19. Drive belt 910 will pass through access tube 912, which will be mounted on a partial cowl component 922, which will be affixed to the main cowl component 920 in a manner that allows at least partial rotation of cowl components 920 and 922, relative to each other.

If desired, drive belt 910 can travel to a powered drive mechanism that is a substantial distance away from the "operating head" of the tool; alternately, a chain-driven or similar mechanical drive mechanism with a powered and rotating non-smooth shaft can be inserted into the system, at a midpoint between the power-supplying drive unit, and the operating head. These and other potentially useful mechanisms have been extensively developed for use in dental tools, and they can be adapted for use as described herein, if desired.

Figure 20:
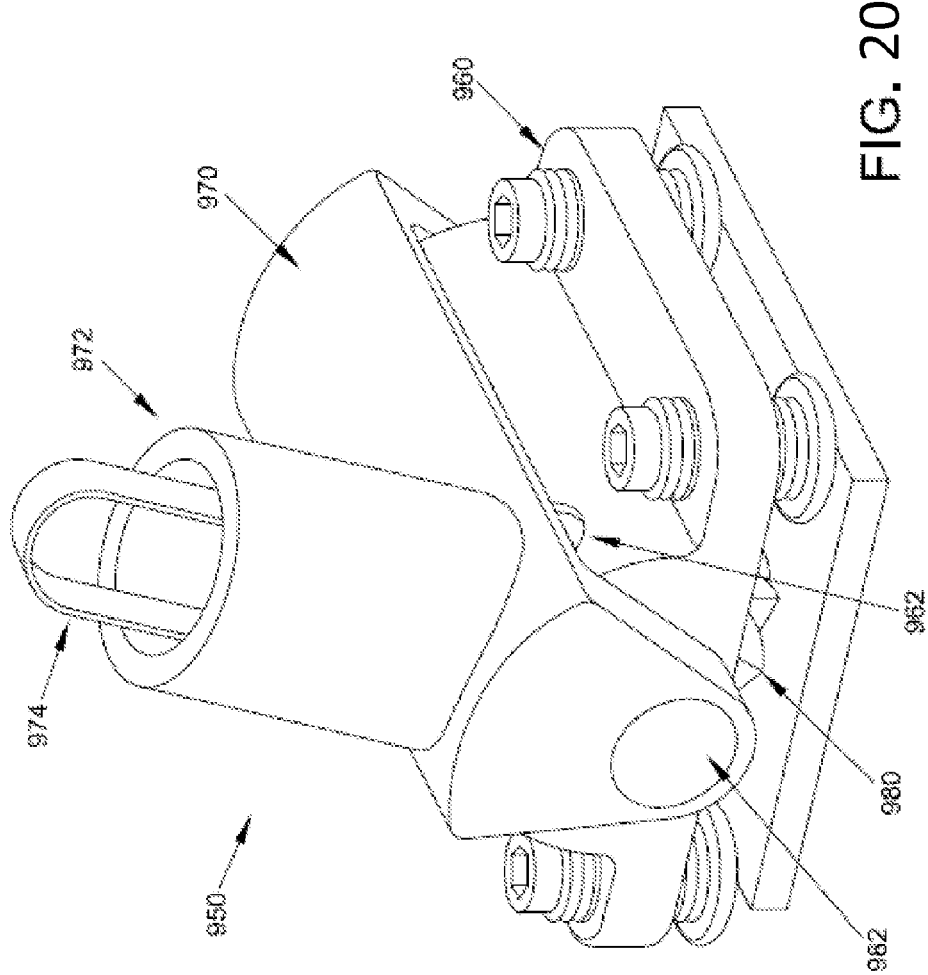
FIG. 20 is a perspective view of a planing tool with a two-part cowl, which allows the top and bottom portions of the cowl to rotate, relative to each other.

FIG. 20 is a perspective view of a third type of planing tool 950 having an alternate design, with a first "lower cowl" component 960 (which can also be called a fixed-foot cowl, a non-rotating cowl, or similar terms), and a second cowl component 970 (which can be called an upper cowl or similar terms). Upper and lower cowl components 960 and 970 can rotate with respect to each other, through a substantial distance or arc. Upper cowl 970 has an access tube 972 affixed to it, while lower cowl 960 has an accommodating slot 962 passing through it. Acting together, these access means allow drive belt 974 to reach and exert tension against rotating shaft 982, which supports grinding burr 980. This will allow the lower cowl 960 and adjustable feet 990 to pass through a substantial arc of travel, relative to access tube 972. Access tube 972 will be constrained fairly tightly, during use, by the requirement that it must pass through a relatively narrow tunnel that passes through the skin and various tendons, ligaments, and other tissues, during an arthroscopic procedure.

FIG. 21 is a side elevation view, which illustrates feet 990 positioned at an extension (height) that will cause the rotating burr 980 to create a flat planar surface. As can be visualized by considering that view, if either or both of two adjustable shafts 992 were extended farther down, while the lower surface of cylindrical burr 980 remains at the same height, tool 950 would create a convex rounded surface, having a controllable radius. Alternately, if either or both of feet 990 were raised slightly, while the lower surface of cylindrical burr 980 remains at the same height, tool 950 would create a concave rounded surface, having a controllable radius. Accordingly, this mechanism can provide the means for creating a controllably rounded surface when desired, such as when a femoral runner surface is being prepared to receive a cartilage implant. As mentioned above, an electromechanical or hydraulic system can be developed if desired, to enable automated and even computer-controlled extension and retraction of the struts 992, which control the heights of feet 990, and shafts 992 can be provided with adjustment mechanisms other than threaded exteriors, such as piston mechanisms, geared systems, linear electric motors, etc.

Guidance and Control Devices and Systems

The surgical tools of this invention can be used in conjunction with any suitable type of securing, guiding, or other control system that is already know or hereafter developed.

As one example, prior to inserting a planing tool into a joint that is being prepared, a set of pins or screws having eyelets at the tops can be inserted into the bone, such as by using small drill holes that later will be enlarged and used to anchor the final implant. Strands of suture material, wire, or similar material can be placed through the eyelets, and secured to several points around the periphery of a planing tool. After the planing tool has been inserted into the joint, the strands can be tightened, and affixed to miniaturized winch-type devices that are affixed to an electromechanical device that will remain outside the joint. The surgeon, with the aid of a computerized control device if desired, can operate the winches in ways that will use tension on the strands, passing through the peripherally-located eyelets inside the joint, to pull the planing tool in any desired direction, across the bone surface that is being prepared.

Other examples of guiding and control mechanisms, which can be used to control the movement of a planing tool across a bone surface, can use, for example, one or more relatively flat and thin curved metallic strips, which will have enough width to avoid flexure in an unwanted direction, while using curvature in desired directions to press a tool against a bone surface with a desired degree of firmness. Such devices are often referred to as templates.

A third class of candidate guidance-and-control devices includes templates that are positioned outside of a joint that is being repaired. For example, pins, struts, or other protrusions on the handles of the tools can slide and move within slots or grooves that have been machined into external templates. Alternately, the external templates can have pins or struts that will slide within grooves or slots that have been machined into the surfaces of the tool handles.

Still another class of candidate guidance-and-control devices includes computer-controlled electromechanical devices (often called "servo-" devices). At a specific stage during an arthroscopic or similar procedure, the computer-controlled holding device will be moved into position, and the base or handle of the tool will be secured within the device. The holding device (and the tool) will travel through a predetermined pathway, using software instructions that were previously loaded into the computer software. For any specific patient, the pathway that the working end of the tool will take will be determined in advance, based on the size and shape of the bone surface being prepared in that patient.

These are several examples of candidate guidance-and-control devices that can be used, if desired, with the planing tools disclosed herein. Such systems are not essential to the use of the tools herein, which generally are designed to enable direct handling and control by surgeons. Accordingly, any such guidance-and-control systems or devices (or other supporting systems or devices) should be regarded as being optional, for use if and when desired, with these new types of tools.

Thus, there has been shown and described a new and useful advance in the design, construction, and use of surgical tools. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

What is claimed is:

1. A surgical tool for planning a surface of a bone while being manipulated, comprising: a handle, with a coupling configured to receive rotational power and suction from a drive unit; a cowl assembly affixed to a working end of the tool opposite from said handle; a grinding burr that is rotatable by said rotational power via the coupling, the grinding burr being mounted within said cowl assembly so as to be movable against the surface of the bone at a first exposed surface region of the grinding burr, and covered by the cowl assembly at a second surface region; wherein the cowl assembly comprises two partial cowls that are relatively rotatable to form a variable sized opening around the grinding burr, using a control at the handle, to adjust a size of the variable sized opening between arc tips of the two partial cowls, and wherein the arc tips are placed to contact the bone surface such that the grinding burr is supported by one or both of the arc tips while planning the bone surface.

2. The surgical tool of claim 1, wherein said grinding burr is rotatable on a driveshaft that passes through said handle to the coupling.

3. The surgical tool of claim 1, wherein said cowl assembly comprises a fixed outer sleeve at the second surface region covering the grinding burr;
   wherein the at least one partial cowl is rotatable around the grinding burr relative to the fixed outer sleeve, using a lever at the handle, to adjust the variable sized opening; and,
   wherein at least said at least one partial cowl has an arc tip that is placed to contact the bone surface such that the grinding burr is supported by the arc tip while the grinding burr is moved over the bone surface during a planing operation.

4. The surgical tool of claim 3, wherein at least one said lever is configured to provide a visual indication of a position of an associated arc tip.

5. The surgical tool of claim 3, further comprising a locking mechanism mounted at the handle and engaging at least one said lever to temporarily fix an associated said arc tip at a desired angular position.

6. The surgical tool of claim 1, wherein the cowl assembly further comprises a fixed outer sleeve part; wherein the two partial cowls are cylindrical and concentric with one another and with the grinding burr; and wherein the arc tips of the two partial cowls are edges that brought together and apart by respective levers; whereby the levers control a width of the variable size opening and also a planing depth of the grinding burr.

7. The surgical tool of claim 1, wherein said handle encloses a suction conduit.

* * * * *